US012213887B2

(12) United States Patent
LaReau

(10) Patent No.: US 12,213,887 B2
(45) Date of Patent: Feb. 4, 2025

(54) DIRECT ANTERIOR HIP REPLACEMENT TROCHANTER SECUREMENT APPARATUS

(71) Applicant: Justin Mark LaReau, Hinsdale, IL (US)

(72) Inventor: Justin Mark LaReau, Hinsdale, IL (US)

( * ) Notice: Subject to any disclaimer, the term of this patent is extended or adjusted under 35 U.S.C. 154(b) by 546 days.

(21) Appl. No.: 17/369,337

(22) Filed: Jul. 7, 2021

(65) Prior Publication Data

US 2022/0008206 A1  Jan. 13, 2022

Related U.S. Application Data

(60) Provisional application No. 63/049,338, filed on Jul. 8, 2020.

(51) Int. Cl.
| | |
|---|---|
| *A61B 17/82* | (2006.01) |
| *A61B 17/04* | (2006.01) |
| *A61B 17/06* | (2006.01) |
| *A61B 17/84* | (2006.01) |
| *A61F 2/36* | (2006.01) |

(52) U.S. Cl.
CPC ........ *A61F 2/3601* (2013.01); *A61B 17/0401* (2013.01); *A61B 17/06166* (2013.01); *A61B 17/842* (2013.01)

(58) Field of Classification Search
CPC ..... A61F 2/30739; A61B 17/74; A61B 17/58; A61B 17/82
See application file for complete search history.

(56) References Cited

U.S. PATENT DOCUMENTS

| | | | | |
|---|---|---|---|---|
| 5,797,916 | A | * | 8/1998 | McDowell ........... A61B 17/842 606/297 |
| 6,066,141 | A | * | 5/2000 | Dall ....................... A61B 17/82 606/907 |
| 6,277,120 | B1 | | 8/2001 | Lawson |
| 7,611,513 | B2 | * | 11/2009 | Deloge ............... A61F 2/30739 606/74 |
| 8,574,235 | B2 | | 11/2013 | Stone |
| 8,764,809 | B2 | | 7/2014 | Lorenz et al. |
| 8,979,940 | B2 | | 3/2015 | Porter et al. |
| 9,730,743 | B2 | | 8/2017 | Vargas et al. |
| 10,201,376 | B2 | | 2/2019 | Cavallazzi et al. |
| 10,278,749 | B2 | | 5/2019 | Jakob et al. |
| 10,675,072 | B2 | * | 6/2020 | Ananthan .......... A61B 17/8004 |
| 2010/0234896 | A1 | | 9/2010 | Lorenz et al. |

(Continued)

OTHER PUBLICATIONS

Image located at http://www.devatibbi.com, available before Jul. 8, 2020.

(Continued)

*Primary Examiner* — Jerrah Edwards
*Assistant Examiner* — Jacob Lee Fincher
(74) *Attorney, Agent, or Firm* — Neal, Gerber & Eisenberg LLP

(57) ABSTRACT

A direct anterior hip replacement trochanter securement apparatus including a trochanter engager, an implant connector configured to securely connect the trochanter engager to an implant in a femur, and a trochanter engager securer configured to securely hold part of the trochanter engager at a point along the femur below the trochanter.

15 Claims, 27 Drawing Sheets

(56) References Cited

U.S. PATENT DOCUMENTS

| | | | |
|---|---|---|---|
| 2013/0304133 A1* | 11/2013 | Trauner | A61B 17/82 |
| | | | 606/301 |
| 2014/0031878 A1 | 1/2014 | Norris et al. | |
| 2014/0107711 A1 | 4/2014 | Norris et al. | |
| 2015/0182266 A1 | 7/2015 | Jakob et al. | |
| 2015/0209093 A1* | 7/2015 | Dallis | A61B 17/8061 |
| | | | 606/281 |
| 2018/0256221 A1 | 9/2018 | Koay et al. | |
| 2019/0380754 A1 | 12/2019 | Wiederkehr et al. | |
| 2020/0129297 A1 | 4/2020 | Haidukewych et al. | |

OTHER PUBLICATIONS

Eto, Shuichi, et al., "The Direct Anterior Approach is Associated With Early Revision Total Hip Arthroplasty", The Journal of Arthroplasty 32 (2017), 1001-1005.

Hamadouche, Moussa, et al., "Reattachment of the Ununited Greater Trochanter Following Total Hip Arthroplasty", The Journal of Bone and Joint Surgery, vol. 85-A No. 7, (Jul. 2003) 1330-1337.

Miller, Larry E., et al., "Does Surgical Approach Affect Outcomes in Total Hip Arthroplasty Through 90 Days of Follow-Up? A Systematic Review With Meta-Analysis", The Journal of Arthroplasty 33 (2018), Nov. 14, 2017, 1296-1302.

Taunton, Michael J., et al., "John Charley Award: Randomized Clinical Trial of Direct Anterior and Miniposterior Approach THA: Which Provides Better Functional Recovery?", Clin Orthop Relat Res (2018) 476, Jan. 17, 2018, 216-229.

Thaler, Martin, et al., "Extension of the Direct Anterior Approach for the Treatment of Periprosthetic Femoral Fractures", The Journal of Arthroplasty 34 (2019), 2449-2453.

* cited by examiner

DIRECT ANTERIOR HIP REPLACEMENT TROCHANTER SECUREMENT APPARATUS

PRIORITY

This application claims priority to and the benefit of U.S. Provisional Patent Application No. 63/049,338, filed Jul. 8, 2020, the entire contents of which are incorporated herein by reference.

BACKGROUND

Articulating joints in the body may become mechanically compromised due to degeneration, disease, and/or trauma. Such articulating joints may be repaired or replaced with surgical intervention of one or both articulating surfaces and underlying bones. Similarly, prior surgical repairs or joint replacement devices employed for articulating joint may sometimes require additional revision surgery. During the course of such surgical interventions, muscle attachments and their bony apophyses may require reconstruction or repair.

Various known implant apparatuses facilitate replacement or repair of such articulating joints. Such known apparatuses frequently remove a portion of the native bony anatomy and replace that native bony anatomy with one or more prosthetic portions. Examples of frequently replaced articulating joints include but are not limited to the hip joint, the knee joint, the elbow joint, and the shoulder joint. The manner in which the surgical intervention occurs often dictates the types of implant apparatus that can be employed.

Articulating hip joints can be replaced through a direct anterior minimally invasive approach. In certain limited situations, an undesired fracture can occur during or as a result of this approach. In one such specific non-limiting example, the bony greater trochanter of the femur may sometimes experience significant deforming force during a direct anterior approach hip replacement surgery. The force may exceed the material strength of the bone and can lead to fracture of the trochanteric bone (sometimes referred to herein as the "trochanter") around the femoral portion of a joint replacing prosthesis. While the bone itself may fracture, there may also exist residual soft tissue attachments to that bone which, if left unopposed, may lead to alteration in the bone location and anatomy, dysfunction of the normal anatomic relationships, and poor healing potential.

If such a fracture occurs, this fracture can be challenging to fix because of anatomic and surgical exposure constraints. Known apparatuses for repair of such fractures are not configured for implementation through an anterior approach during a direct anterior approach hip replacement surgery.

Accordingly, there is a need for an apparatus that can be used for repair of such trochanter fractures during a direct anterior approach hip replacement surgery.

SUMMARY

Various embodiments of the present disclosure relate to apparatus and methods including surgical implant and methods of employing such surgical implants that address the above described needs. Various embodiments of the present disclosure provide direct anterior hip replacement trochanter securement apparatuses and methods that can be employed during a direct anterior approach hip replacement surgery either for repair of a fracture of the bony greater trochanter of the femur or for minimizing the likelihood of a subsequent fracture of the bony greater trochanter of the femur.

Generally, the various embodiments of apparatus of the present disclosure facilitate, when needed, fixation for peri-prosthetic fractures of the femoral bone during anterior approach hip replacement surgery. More specifically, the various embodiments of the apparatus of the present disclosure prevent the clinical sequalae of trochanteric non-union and/or escape following a peri-prosthetic greater trochanteric fracture sustained during anterior approach total hip replacement or thereafter. Various embodiments of the trochanter securement apparatus of the present disclosure facilitate bony fixation, maintain fragment healing position, and preserve abductor motion to facilitate optimal post-procedure healing and patient function.

Various embodiments of the trochanter securement apparatus of the present disclosure facilitate the implant application through the direct anterior approach, and specifically are configured to function, when needed, with various implants used in a direct anterior approach, and do not need to be employed with such various implants when not needed. In other words, various embodiments of the trochanter securement apparatus of the present disclosure do not interfere at all or change the function of the implants that such trochanter securement apparatus can be employed with, and thus the trochanter securement apparatus can be employed when an undesired fracture occurs during a direct anterior approach hip replacement surgery or that may occur thereafter, but does not need to be employed when such an undesired facture does not occur (or the surgeon does not desire to provide the added support and functionality for the femur bone provided by the trochanter securement apparatus).

Various embodiments of the present disclosure provide a direct anterior hip replacement trochanter securement apparatus including: (1) a trochanter engager; (2) an implant connector configured to securely connect part of the trochanter engager to an implant in a femur; and (3) a trochanter engager securer configured to securely hold part of the trochanter engager at a point along the femur below the trochanter.

Various embodiments of the present disclosure provide various different tools for positioning and attaching various trochanter securement apparatus of the present disclosure via a direct anterior approach.

Other objects, features, and advantages of the present disclosure will be apparent from the following detailed disclosure and accompanying drawings.

DETAILED DESCRIPTION

Figure 1:
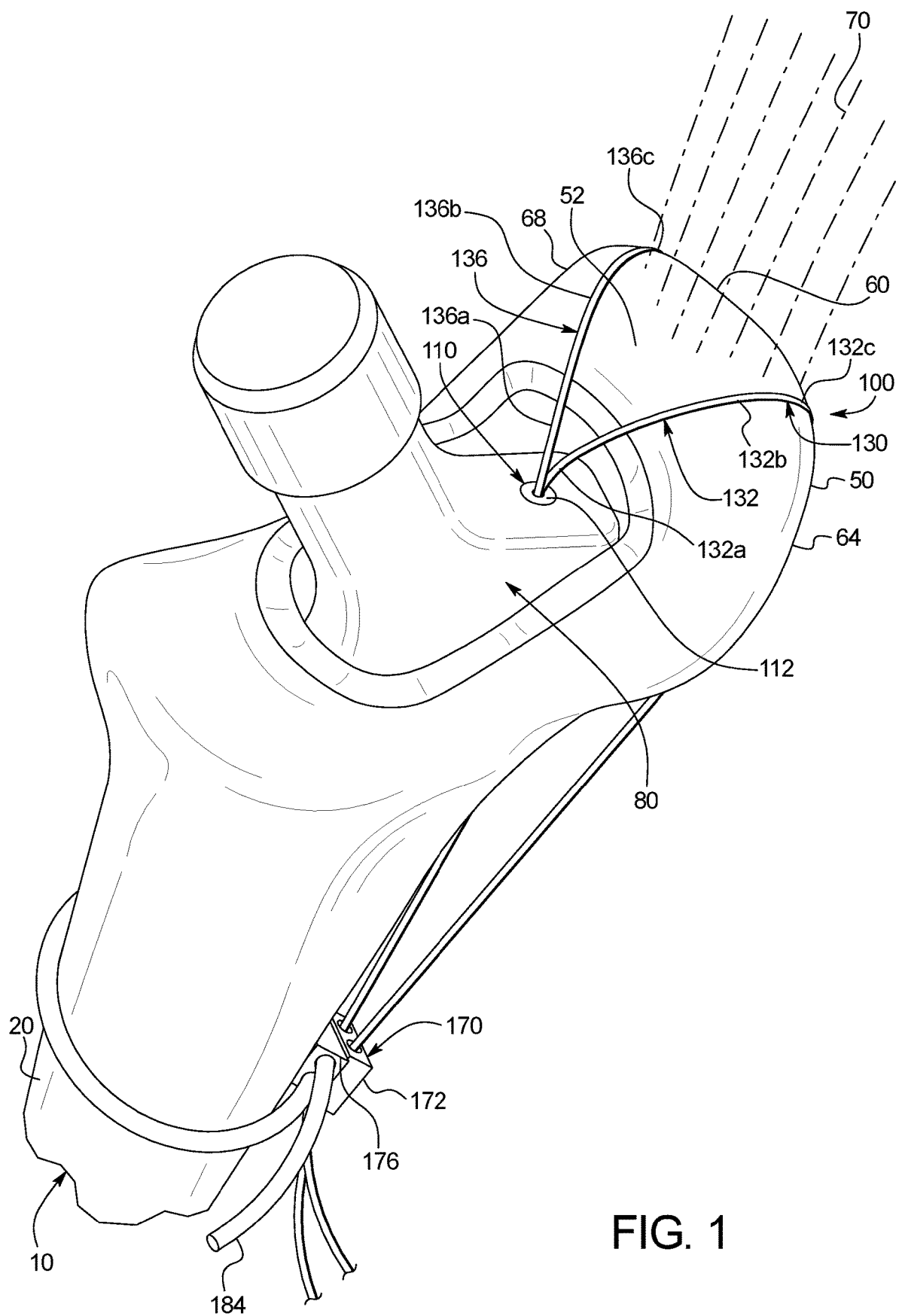
FIG. 1 is a fragmentary anterolateral perspective view of an upper portion of a femur (including the trochanter), a portion of part of an implant shown inserted into the femur, and a trochanter securement apparatus of one example embodiment of the present disclosure, and showing this example trochanter securement apparatus secured to the implant and secured to the femur.

While the systems, devices, and methods described herein may be embodied in various forms, the drawings show and the specification describes certain exemplary and non-limiting embodiments. Not all components shown in the drawings and described in the specification may be required, and certain implementations may include additional, different, or fewer components. Variations in the arrangement and type of the components; the shapes, sizes, and materials of the components; and the manners of connections of the components may be made without departing from the spirit or scope of the claims. Unless otherwise indicated, any directions referred to in the specification reflect the orientations of the components shown in the corresponding drawings and do not limit the scope of the present disclosure. Further, terms that refer to mounting methods, such as mounted, connected, etc., are not intended to be limited to direct mounting methods but should be interpreted broadly to include indirect and operably mounted, connected, and like mounting methods. This specification is intended to be taken as a whole and interpreted in accordance with the principles of the present disclosure and as understood by one of ordinary skill in the art.

Turning now to the figures, FIGS. 1 to 14 and 22 to 25 illustrate different example embodiments of the direct anterior hip replacement trochanter securement apparatus of the present disclosure. Each example embodiment is shown after that example direct anterior hip replacement trochanter securement apparatus has been secured to the femur 10 and to the implant 80 that is inserted in the femur 10. In each example, the femur 10 includes an intermediate portion 20 of the femur 10 below the trochanter 50 of the femur 10. The trochanter 50 generally includes, when the femur 10 and the hip are returned to their normal anatomic positions after surgery: (1) a medial interior portion 52, (2) a lateral portion 56, (3) an anterior portion 64, (4) a posterior portion 68, and (5) a superior portion 60. Various muscles are attached to the femur 10 and specifically the trochanter 50. Certain of these various muscles extending from the trochanter 50 are generally indicated by phantom lines 70. These phantom lines are not meant to show the exact or all of the muscles attached to the trochanter 50, but rather are provided as a general representation of certain of these muscles.

Each example embodiment of the direct anterior hip replacement trochanter securement apparatus can be employed during a direct anterior approach hip replacement surgery either for repair of a fracture of the bony greater trochanter of the femur or for minimizing the likelihood of a subsequent fracture of the bony greater trochanter of the femur. Each example embodiment of the direct anterior hip replacement trochanter securement apparatus facilitates bony fixation, maintains fragment healing position, and preserves abductor motion to facilitate optimal post-procedure healing and patient function. Each example embodiment of the direct anterior hip replacement trochanter securement apparatus does not interfere at all or change the function of the implants. Each example embodiment of the direct anterior hip replacement trochanter securement apparatus minimizes interference with the muscles attached to the femur.

Various embodiments of the present disclosure provide a direct anterior hip replacement trochanter securement apparatus including: (1) a trochanter engager; (2) an implant connector configured to securely connect part of the trochanter engager to an implant in a femur; and (3) a trochanter engager securer configured to securely hold part of the trochanter engager at a point along the femur below the trochanter. Various such embodiments engage various different combinations of the medial interior portion 52, the lateral portion 56, the superior portion 60, the anterior portion 64, and the posterior portion 68, of the trochanter 50. Various example embodiments including such components are further discussed below; but these example embodiment are not meant to limit the scope of the present disclosure.

Figure 1A:
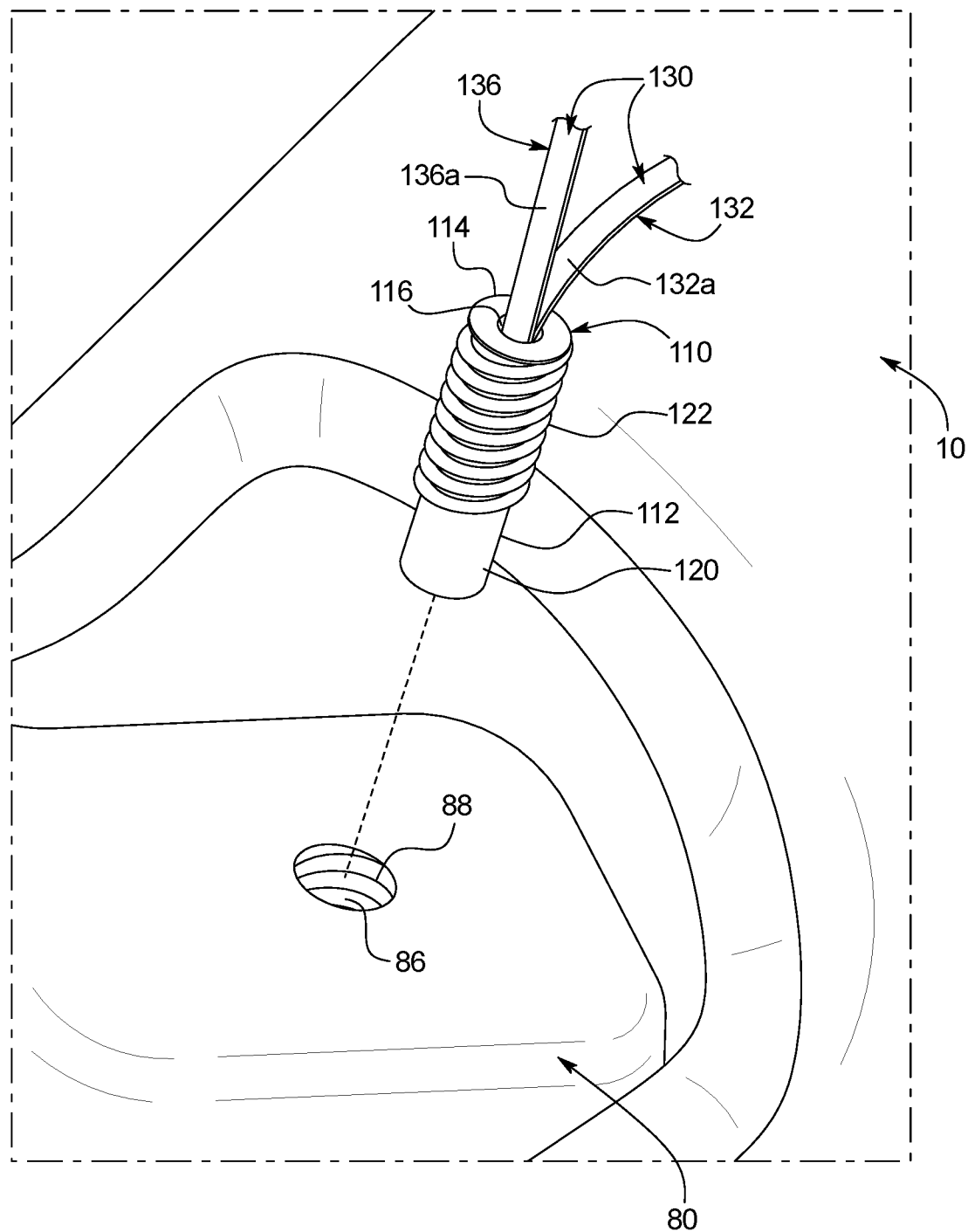
FIG. 1A is an enlarged perspective view of part of the upper portion of the femur of FIG. 1 (including part of the trochanter), a portion of part of the implant of FIG. 1, and an implant connector and parts of the tape-shaped sutures of the trochanter securement apparatus of FIG. 1 prior to attachment of the implant connector to the implant.
Figure 2:
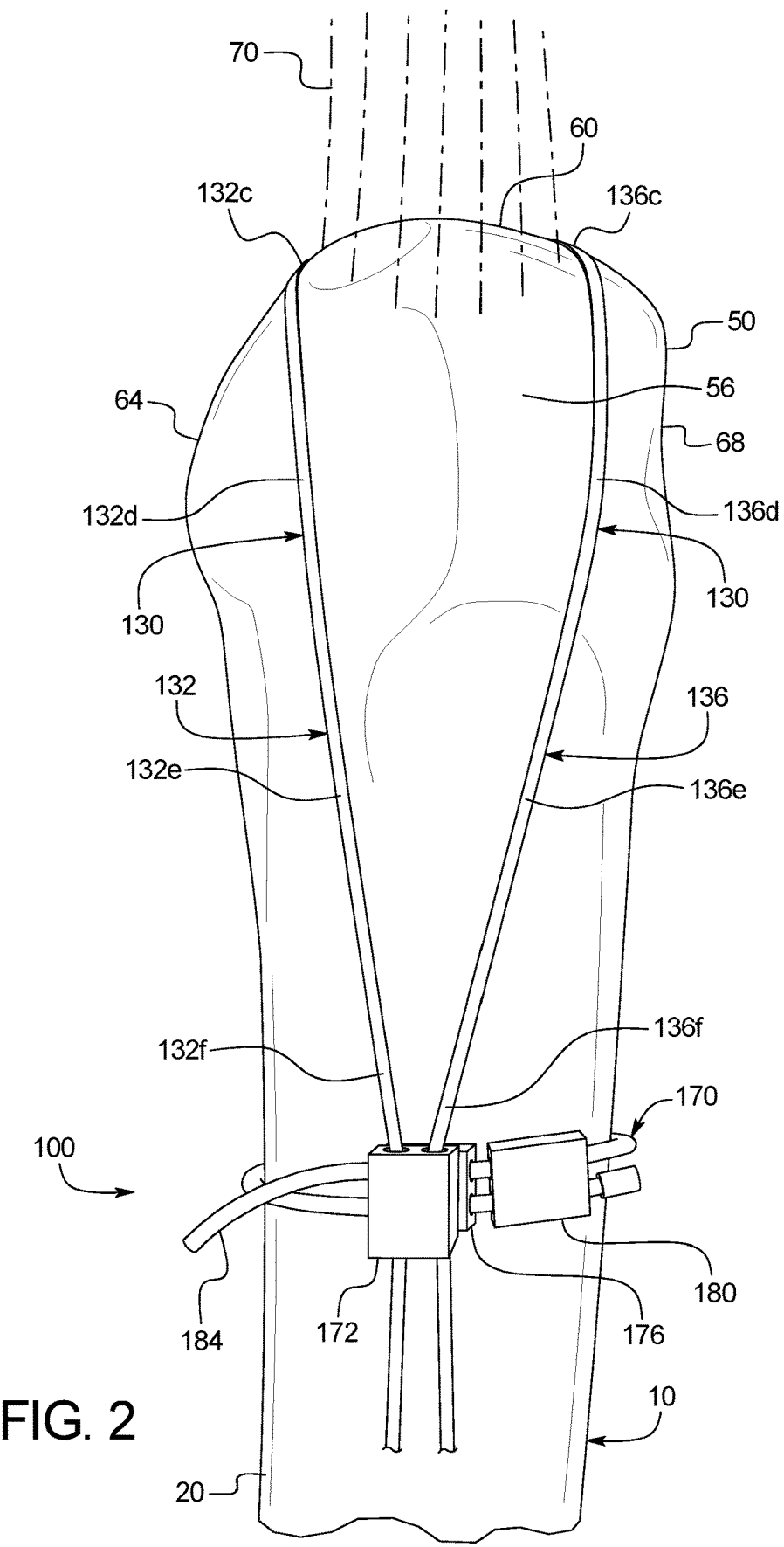
FIG. 2 is a fragmentary lateral perspective view of the upper portion of the femur (including the trochanter) of FIG. 1 and the trochanter securement apparatus of FIG. 1, and showing this example trochanter securement apparatus secured to the femur.

FIGS. 1, 1A, and 2 illustrate one example embodiment of a direct anterior hip replacement trochanter securement apparatus of the present disclosure. This example direct anterior hip replacement trochanter securement apparatus is generally indicated by numeral 100, and is referred to herein for brevity as the trochanter securement apparatus 100 or the apparatus 100. This example trochanter securement apparatus 100 generally includes: (1) an implant connector 110; (2) a trochanter engager 130; and (3) a trochanter engager securer 170.

More specifically, in this example embodiment, the implant connector 110 includes a fastener 112 removably connectable to the implant 80. The implant 80 defines an opening 86 and has inner threads 88 extending into that opening 86. In this example, the fastener 112 includes a head 114 and a shaft 120 extending from the head 114. The shaft 120 includes outer threads 122. The head 114 and the shaft 120 define a central opening 116 through which first end portions of parts of the trochanter engager 130 extends, as further described below. The outer threads 122 of the shaft 120 are configured to engage the inner threads 88 when the shaft 120 is inserted into the opening 86 defined by the implant 80 such that the fastener 112 can be threadably received in and secured to the implant 80. In this example embodiment, the fastener 112 is made from metal such as a titanium alloy to allow for minimize galvanic corrosion; however, it should be appreciated that the fastener 112 can be made from other suitable materials in accordance with the present disclosure. It should also be appreciated that the fastener can be otherwise suitably configured and sized in accordance with the present disclosure.

In this example embodiment, the trochanter engager 130 includes a first suture 132 and a second suture 136. The first suture 132 and the second suture 136 are both elongated flat flexible members. The first suture 132 includes: (a) a first section 132a; (b) a second section 132b; (c) a third section 132c; (d) a fourth section 132d; (e) a fifth section 132e; and (f) a sixth section 132f. Likewise, the second suture 136 includes: (a) a first section 136a; (b) a second section 136b; (c) a third section 136c; (d) a fourth section 136d; (e) a fifth section 136e; and (f) a sixth section 136f.

The first section 132a of the first suture 132 and the first section 136a of the second suture 136 are respective end sections and are securely attached to the fastener 112. Specifically, in this example embodiment, the first section 132a of the first suture 132 and the first section 136a of the second suture 136 extend through the opening in the fastener 112 and are integrally suitably attached to the inner wall of the fastener 112.

The second section 132b of the first suture 132 and the second section 136b of the second suture 136 are respective intermediate sections and are configured to engage the medial interior portion 52 of the trochanter 50.

The third section 132c of the first suture 132 and the third section 136c of the second suture 136 are respective intermediate sections and are configured to engage the superior portion 60 of the trochanter 50.

The fourth section 132d of the first suture 132 and the fourth section 136d of the second suture 136 are respective intermediate sections and are configured to engage the lateral portion 56 of the trochanter 50.

The fifth section 132e of the first suture 132 and the fifth section 136e of the second suture 136 are respective intermediate sections and are configured to extend downwardly toward the trochanter engager securer 170.

The sixth section 132f of the first suture 132 and the sixth section 136f of the second suture 136 are respective end sections and are securely attached to the trochanter engager securer 170. Specifically, in this example embodiment, the sixth section 132f of the first suture 132 and the sixth section 136*f* of the second suture 136 extend through the openings in the trochanter engager securer 170 and are securely attached thereto. Such sutures 132 and 136 can be tied into a knot or otherwise suitably connected after being inserted though the suture receiver 172 (described below). In other embodiments, a suitable a cleat-type device can be employed for this purpose. In alternative embodiments of the present disclosure where cables are employed instead of suture, the cables can be crimped by the trochanter engager securer 170.

The first section 132*a* of the first suture 132, the first section 136*a* of the second suture 136, the fifth section 132*e* of the first suture 132, the fifth section 136*e* of the second suture 136, the sixth section 132*f* of the first suture 132, and the sixth section 136*f* of the second suture 136 collectively function to maintain the second section 132*b* of the first suture 132, the second section 136*b* of the second suture 136, the third section 132*c* of the first suture 132, the third section 136*c* of the second suture 136, the fourth section 132*d* of the first suture 132, and the fourth section 136*d* of the second suture 136 in engagement with those various portions of the trochanter 50 and to limit movement of the first and second sutures 132 and 136 with respect to the trochanter 50. Accordingly, the second section 132*b* of the first suture 132, the second section 136*b* of the second suture 136, the third section 132*c* of the first suture 132, the third section 136*c* of the second suture 136, the fourth section 132*d* of the first suture 132, and the fourth section 136*d* of the second suture 136 collectively function to respectively engage the various portions of the trochanter 50 to: (a) provide support for the trochanter 50; (b) provide a link between the implant 80 and various distal points of the trochanter 50 to repair muscle or bone attachments; (d) provide oppose deforming forces to the soft tissue attachments of any fractured portion of the trochanter 50; (e) restore anatomic configuration of the trochanter 50; and (f) maintain a mechanical environment to facilitate healing of the trochanter 50.

In this example embodiment, the first suture 132 and the second suture 136 are each made from braided polyester; however, it should be appreciated that the first suture 132 and the second suture 136 can be made from other suitable materials in accordance with the present disclosure. It should also be appreciated that: (1) the first suture 132 and the second suture 136 can be otherwise suitably configured and sized in accordance with the present disclosure; (2) the first suture 132 and the second suture 136 are identical in this example embodiment but can be different in accordance with the present disclosure; (3) the quantity of sutures can vary in accordance with the present disclosure; and (4) the quantity of sections of the sutures and the specific functions of those sections of the sutures can vary in accordance with the present disclosure.

In this example embodiment, the trochanter engager securer 170 includes: (1) suture receiver 172; (2) a first cable receiver 176 connected to the suture receiver 172; (3) a second cable receiver 180; and (4) a cable 184. The suture receiver 172 is configured to receive and securely hold the sutures 132 and 136 inserted through the openings (not labeled) in the suture receiver 172. The sutures 132 and 136 can be tie in a knot on the lower side of the suture receiver 172 or otherwise attached as described above. The first cable receiver 176, the second cable receiver 180, and the cable 184 are configured to co-act in a suitable manner to securely connect the trochanter engager securer 170 to the femur 10. In various embodiments, a suitable tool can be used to pull the sutures 132 and 136 through the suture receiver 172. Such as tool (not shown) can have a loop inserted through the suture receiver 172 to grab the sutures and pull them through the suture receiver 172. The sutures can be spaced apart by a tubular conduit to facilitate suture spacing and appropriate vector of tensile force.

Figure 21:
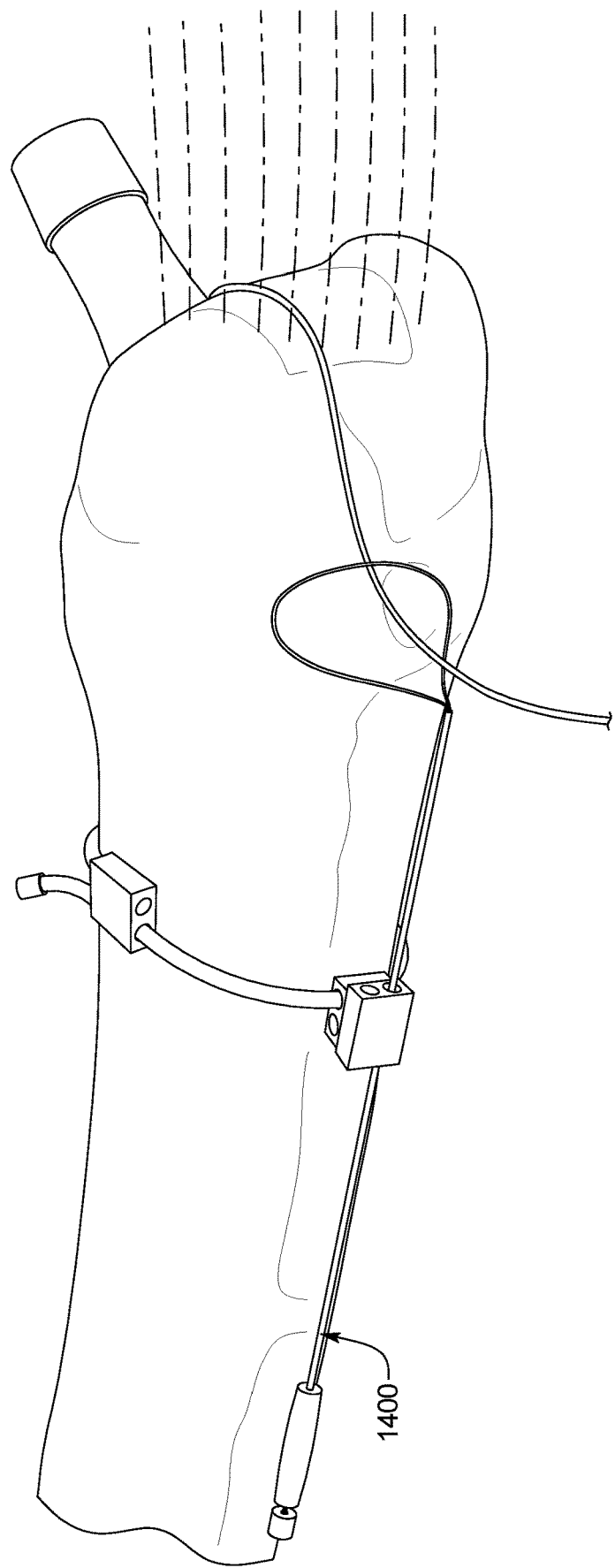
FIG. 21 is a perspective view showing another example tool of the present disclosure usable to attach a trochanter securement apparatus to a trochanter.

It should be appreciated that the positions of the suture receiver 172 and the first cable receiver 176 can be switched (such as shown in FIGS. 22, 23, 24, and 25) to bring the sutures closer to the posterior side of the femur (including the trochanter). It should also be appreciated that one end of the cable 184 can have a bead (such as shown in FIG. 21) for engagement with the second cable receiver 180. It should also be appreciated that the stacks of the two sleeves distally can be reversed or otherwise suitably formed. It should also be appreciated that the second cable receiver 180 can be alternatively positioned such as on the opposite side of the femur (such as shown in FIGS. 22, 23, 24, and 25). It should further be appreciated that the trochanter engager securer 170 can be positioned closer to the trochanter (such as shown in FIGS. 22, 23, 24, and 25) to bring the sutures closer to the posterior side of the femur (including the trochanter).

In this example embodiment, the trochanter engager securer 170 is made from titanium alloys; however, it should be appreciated that the trochanter engager securer 170 can be made from other suitable materials in accordance with the present disclosure. It should also be appreciated that the trochanter engager securer 170 can be otherwise suitably configured and sized in accordance with the present disclosure.

FIGS. 1 and 2 show the trochanter securement apparatus 100 after this apparatus 100 has be secured to the femur 10 and to the implant 80 that is inserted in the femur 10. More specifically, FIGS. 1 and 2 show the apparatus 100 after the implant connector 110 has been securely connected to the implant 80, after the trochanter engager 130 has been positioned to engage the trochanter 30 of the femur 10, after the trochanter engager securer 170 has been attached to an intermediate portion 20 of the femur 10 below the trochanter 50, and after the trochanter engager 130 has been securely connected to the trochanter engager securer 170. This example embodiment can be employed for smaller or less significant fractures or to prevent fractures, where the sutures function as tensioning bands. This example embodiment is flexible in its installation and use, and can be seated in various different positions (such as high or low positions). This example embodiment is also relatively simple and inexpensive to manufacture.

Figure 3:
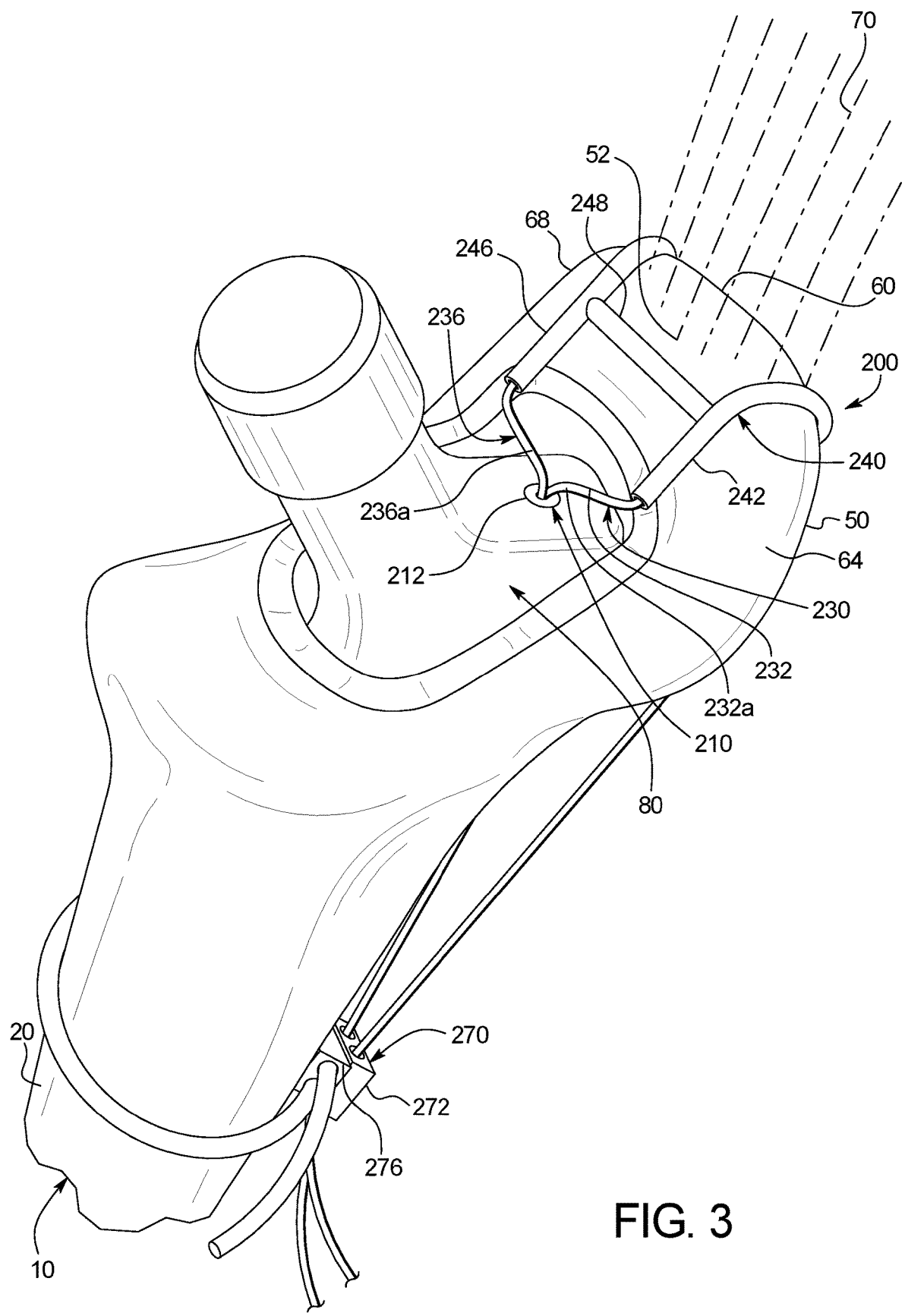
FIG. 3 is a fragmentary anterolateral perspective view of an upper portion of a femur (including the trochanter), a portion of part of an implant shown inserted into the femur, and a trochanter securement apparatus of another example embodiment of the present disclosure, and showing this example trochanter securement apparatus secured to the implant and secured to the femur.
Figure 4:
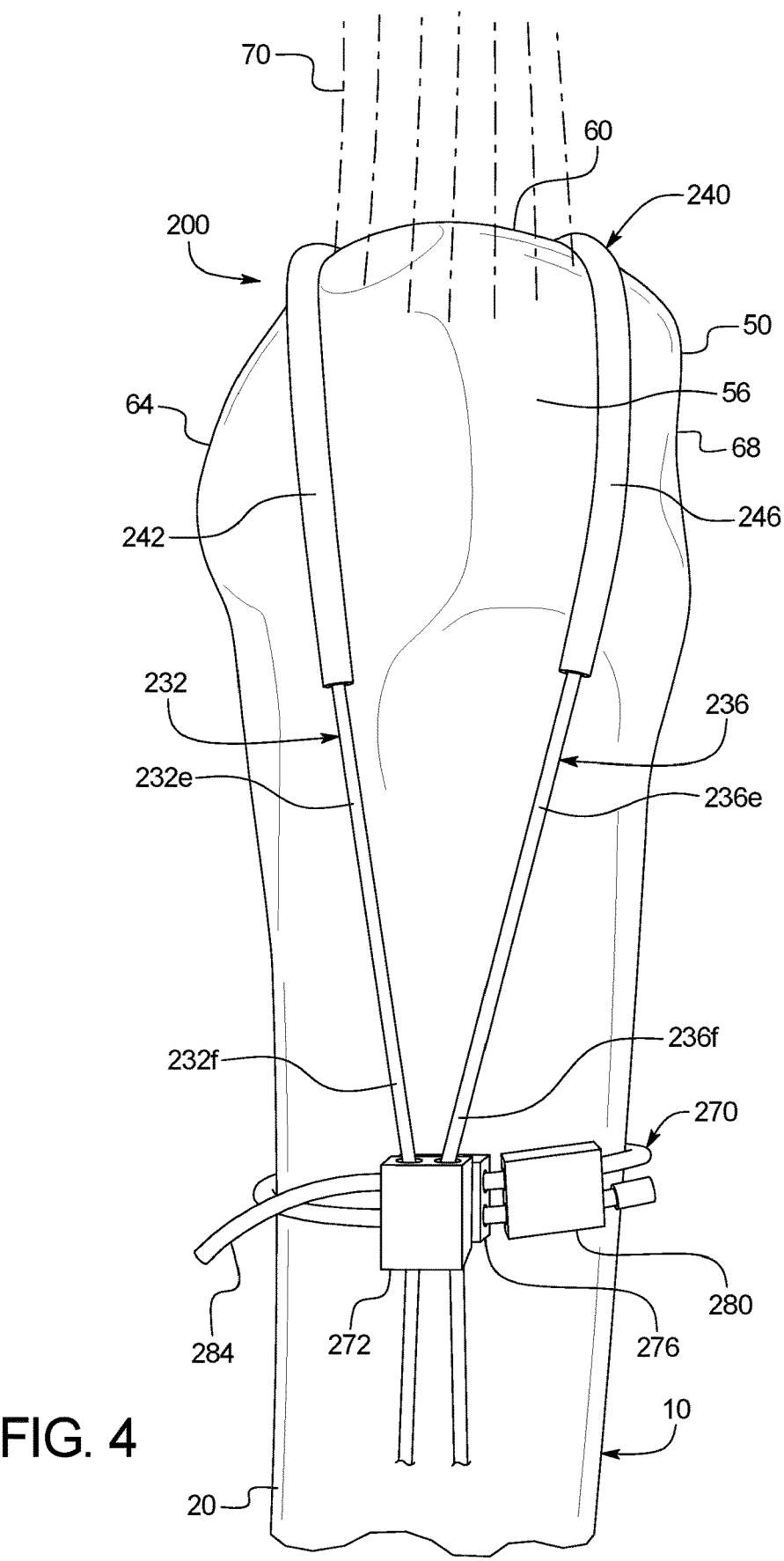
FIG. 4 is a fragmentary lateral perspective view of the upper portion of the femur (including the trochanter) of FIG. 3 and the trochanter securement apparatus of FIG. 3, and showing this example trochanter securement apparatus secured to the femur.

FIGS. 3 and 4 illustrate another example embodiment of a direct anterior hip replacement trochanter securement apparatus of the present disclosure. This example direct anterior hip replacement trochanter securement apparatus is generally indicated by numeral 200, and is referred to herein for brevity as the trochanter securement apparatus 200 or the apparatus 200. This example trochanter securement apparatus 200 generally includes: (1) an implant connector 210; (2) a trochanter engager 230; and (3) a trochanter engager securer 270.

More specifically, in this example embodiment, the implant connector 210 includes a fastener 212 removably connectable to the implant 80. The fastener 210 in this example embodiment is identical to the fastener 110 explained above and is thus not described again for brevity. In this example embodiment, the fastener 212 is made from a titanium alloy; however, it should be appreciated that the fastener 212 can be made from other suitable materials in accordance with the present disclosure. It should also be appreciated that the fastener can be otherwise suitably configured and sized in accordance with the present disclosure.

In this example embodiment, the trochanter engager 230 includes a first suture 232, a second suture 236, and a trochanter gripper 240. The first suture 232 and the second suture 236 are configured to extend through the trochanter gripper 240 and to hold the trochanter engager 230 in place.

The first suture 232 and the second suture 236 are both elongated flat flexible members. The first suture 232 includes: (a) a first section 232a; (b) a second section (not shown); (c) a third section (not shown); (d) a fourth section (not shown); (e) a fifth section 232e; and (f) a sixth section 232f. Likewise, the second suture 236 includes: (a) a first section 236a; (b) a second section (not shown); (c) a third section (not shown); (d) a fourth section (not shown); (e) a fifth section 236e; and (f) a sixth section 236f.

In this example embodiment, the trochanter gripper 240 is configured to engage each of the medial interior portion 52, the superior portion 60, and the lateral portion 56 of the trochanter 50. The trochanter gripper 240 includes a first tube 242, a second tube 246, and a connector 248 that suitably connects the first tube 242 and the second tube 246. The first tube 242 and the second tube 246 each define internal suture passageways (not shown or labeled) through which the respective sutures 232 and 236 can be threaded through. The trochanter gripper 240 and specifically the first tube 242, the second tube 246, and the connector 248 provide increased engagement surface areas for engagement with the medial interior portion 52, the superior portion 60, and the lateral portion 56 of the trochanter 50. It should also be noted that the connecter 248 is positioned such that it does not interfere with the muscle 70. In other words, the tubes 242 and 246 and the connector 248 define a space for the muscles 70 and specifically the abductor muscles.

Similar to the above described first embodiment, the first section 232a of the first suture 232 and the first section 236a of the second suture 236 are respective end sections and are securely attached to the implant connector as described above.

The second section of the first suture 232 and the second section of the second suture 236 are respective intermediate sections and are configured to extend through respective anterior portions of the first tube 242 and the second tube 246 of the trochanter gripper 240.

The third section of the first suture 232 and the third section of the second suture 236 are respective intermediate sections and are configured extend through respective top portions the first tube 242 and the second tube 246 of the trochanter gripper 240.

The fourth section of the first suture 232 and the fourth section of the second suture 236 are respective intermediate sections and are configured to extend through respective posterior portions of the trochanter gripper 240.

Similar to the above described first embodiment, the fifth section 232e of the first suture 232 and the fifth section 236e of the second suture 236 are respective intermediate sections and are configured to extend downwardly toward the trochanter engager securer 270.

Similar to the above described first embodiment, the sixth section 232f of the first suture 232 and the sixth section 236f of the second suture 236 are respective end sections and are securely attached to the trochanter engager securer 270. Like the above embodiment, in this example embodiment, the sixth section 232f of the first suture 232 and the sixth section 236f of the second suture 236 extend through the openings in the trochanter engager securer 270 and are securely attached thereto.

The first section 232a of the first suture 232, the first section 236a of the second suture 236, the fifth section 232e of the first suture 232, the fifth section 236e of the second suture 236, the sixth section 232f of the first suture 232, and the sixth section 236f of the second suture 236 collectively function to maintain the second section of the first suture 232, the second section of the second suture 236, the third section of the first suture 232, the third section of the second suture 236, the fourth section of the first suture 232, and the fourth section of the second suture 236 in the first tube 242 and the second tube 246 of the trochanter gripper 240 and to limit movement of the trochanter gripper 270 with respect to the trochanter 50. Accordingly, the second section of the first suture 232, the second section of the second suture 236, the third section of the first suture 232, the third section of the second suture 236, the fourth section of the first suture 232, and the fourth section of the second suture 236 collectively function to respectively cause the first tube 242 and the second tube 246 of the trochanter gripper 240 to engage the various portions of the trochanter 50 to: (a) provide support for the trochanter 50; (b) provide a link between the implant 80 and various distal points of the trochanter 50 to repair muscle or bone attachments; (d) provide oppose deforming forces to the soft tissue attachments of any fractured portion of the trochanter 50; (e) restore anatomic configuration of the trochanter 50; and (f) maintain a mechanical environment to facilitate healing of the trochanter 50.

In this example embodiment, the first suture 232 and the second suture 236 are each made from braided polyester; however, it should be appreciated that the first suture 232 and the second suture 236 can be made from other suitable materials in accordance with the present disclosure. It should also be appreciated that: (1) the first suture 232 and the second suture 236 can be otherwise suitably configured and sized in accordance with the present disclosure; (2) the first suture 232 and the second suture 236 are identical in this example embodiment but can be different in accordance with the present disclosure; (3) the quantity of sutures can vary in accordance with the present disclosure; and (4) the quantity of sections of the sutures and the specific functions of those sections of the sutures can vary in accordance with the present disclosure.

In this example embodiment, the trochanter gripper 240 is made from titanium alloys; however, it should be appreciated that the trochanter gripper 240 can be made from other suitable materials in accordance with the present disclosure. It should also be appreciated that: (1) the trochanter gripper 240 can be otherwise suitably configured and sized in accordance with the present disclosure; (2) the quantity of tubes of the trochanter gripper 240 can be vary in accordance with the present disclosure; (3) the quantity of sutures configured to engage the trochanter gripper 240 can vary in accordance with the present disclosure; (4) the engagement of the sutures with the trochanter gripper 240 can vary in accordance with the present disclosure; and (5) the caliber or diameter of the tubes can also vary in relative scale to the sutures.

In this example embodiment, the trochanter engager securer 270 includes: (1) suture receiver 272; (2) a first cable receiver 276; (3) a second cable receiver 280; and (4) a cable 284. The trochanter engager securer 270 in this example embodiment is identical to the trochanter engager securer 170 explained above and is thus not described again for brevity.

It should be appreciated that the positions of the suture receiver 272 and the first cable receiver 276 can be switched (such as shown in FIGS. 22, 23, 24, and 25) to bring the sutures closer to the posterior side of the femur (including the trochanter). It should also be appreciated that one end of the cable 284 can have a bead (such as shown in FIG. 21) for engagement with the second cable receiver 280. It should also be appreciated that the second cable receiver 280 can be alternatively positioned such as on the opposite side of the femur (such as shown in FIGS. 22, 23, 24, and 25). It should further be appreciated that the trochanter engager securer 270 can be positioned closer to the trochanter (such as shown in FIGS. 22, 23, 24, and 25) to bring the sutures closer to the posterior side of the femur (including the trochanter).

In this example embodiment, the trochanter engager securer 270 is made from titanium alloys; however, it should be appreciated that the trochanter engager securer 270 can be made from other suitable materials in accordance with the present disclosure. It should also be appreciated that the trochanter engager securer 270 can be otherwise suitably configured and sized in accordance with the present disclosure.

FIGS. 3 and 4 show the trochanter securement apparatus 200 after this apparatus 200 has be secured to the femur 10 and to the implant 80 that is inserted in the femur 10. More specifically, FIGS. 3 and 4 show the apparatus 200 after the implant connector 210 has been securely connected to the implant 80, after the trochanter engager 230 including the trochanter gripper 240 has been positioned to engage the trochanter 30 of the femur 10, after the trochanter engager securer 270 has been attached to an intermediate portion 20 of the femur 10 below the trochanter 50, and after the trochanter engager 230 has been securely connected to the trochanter engager securer 270. This example embodiment can be employed for smaller or more significant fractures or to prevent fractures, where the sutures 232 and 236 and the trochanter gripper 240 function together on the trochanter. This example embodiment is also easy to install and use, and can be seated in various different positions. It should be appreciated that the example embodiment can be particularly suited for softer bones. This example embodiment is also relatively simple and inexpensive to manufacture. Under certain surgical circumstances, the sutures 232 and 236 will be mechanically tensioned such that a compressive force is applied across the fracture site, opposing the direct pull of muscles such as muscles 70.

Figure 5:
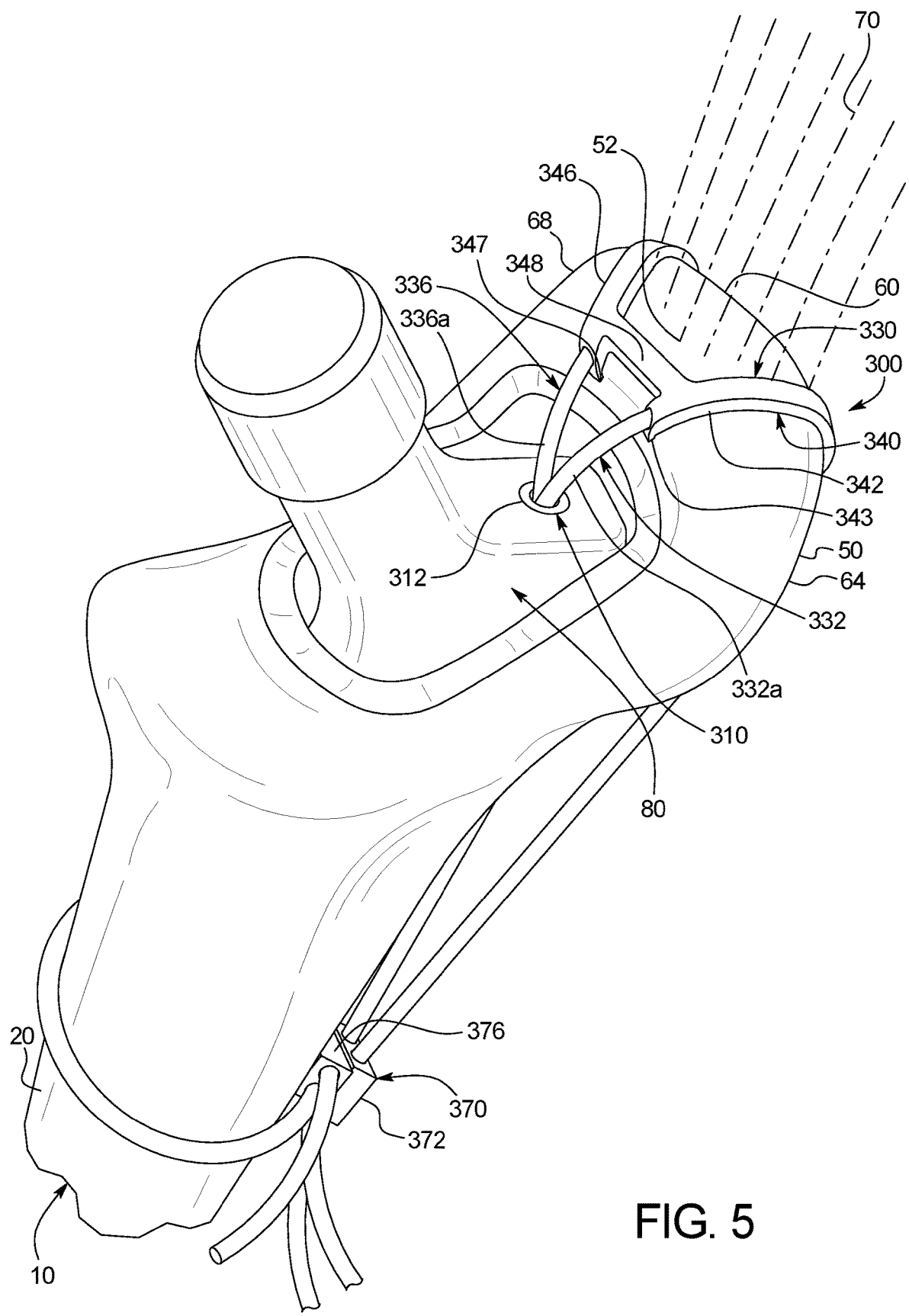
FIG. 5 is a fragmentary anterolateral perspective view of an upper portion of a femur (including the trochanter), a portion of part of an implant shown inserted into the femur, and a trochanter securement apparatus of another example embodiment of the present disclosure, and showing this example trochanter securement apparatus secured to the implant and secured to the femur.
Figure 6:
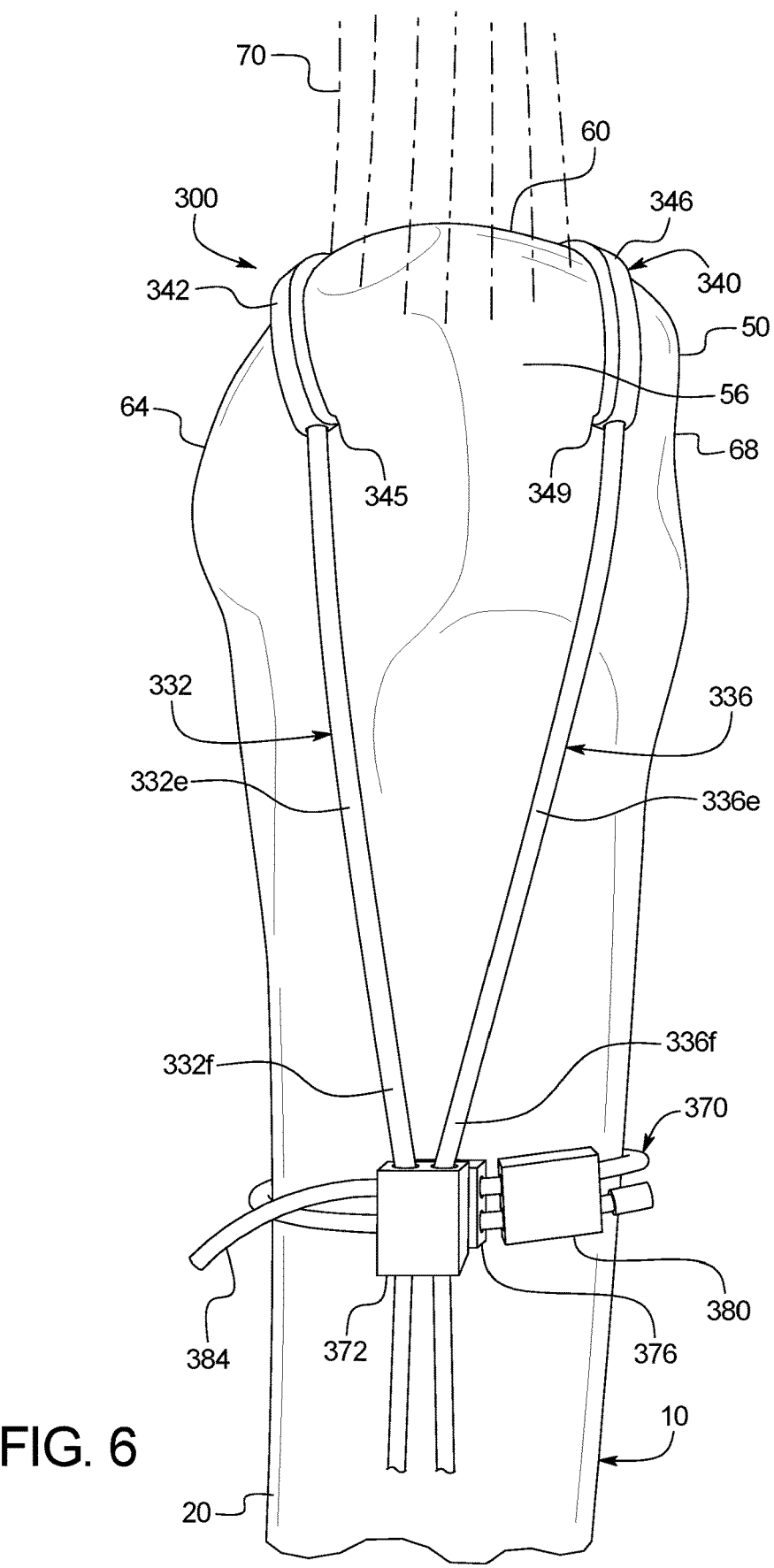
FIG. 6 is a fragmentary lateral perspective view of the upper portion of the femur (including the trochanter) of FIG. 5 and the trochanter securement apparatus of FIG. 5, and showing this example trochanter securement apparatus secured to the femur.

FIGS. 5 and 6 illustrate another example embodiment of a direct anterior hip replacement trochanter securement apparatus of the present disclosure. This example direct anterior hip replacement trochanter securement apparatus is generally indicated by numeral 300, and is referred to herein for brevity as the trochanter securement apparatus 300 or the apparatus 300. This example trochanter securement apparatus 300 generally includes: (1) an implant connector 310; (2) a trochanter engager 330; and (3) a trochanter engager securer 370.

More specifically, in this example embodiment, the implant connector 310 includes a fastener 312 removably connectable to the implant 80. The fastener 312 in this example embodiment is identical to the fastener 110 explained above and is thus not described again for brevity. In this example embodiment, the fastener 312 is made from a titanium alloy; however, it should be appreciated that the fastener 312 can be made from other suitable materials in accordance with the present disclosure. It should also be appreciated that the fastener can be otherwise suitably configured and sized in accordance with the present disclosure.

In this example embodiment, the trochanter engager 330 includes a first suture 332, a second suture 336, and a trochanter gripper 340. The first suture 332 and the second suture 336 are configured to extend through the trochanter gripper 340 and to hold the trochanter engager 330 in place.

The first suture 332 and the second suture 336 are both elongated flat flexible members. The first suture 332 includes: (a) a first section 332a; (b) a second section (not shown); (c) a third section (not shown); (d) a fourth section (not shown); (e) a fifth section 332e; and (f) a sixth section 332f. Likewise, the second suture 336 includes: (a) a first section 336a; (b) a second section (not shown); (c) a third section (not shown); (d) a fourth section (not shown); (e) a fifth section 336e; and (f) a sixth section 336f.

In this example embodiment, the trochanter gripper 340 is configured to engage each of the medial interior portion 52, the superior portion 60, and the lateral portion 56 of the trochanter 50. The trochanter gripper 340 includes a first tube 342, a second tube 346, and a connector 348 that suitably connects the first tube 342 and the second tube 346. The first tube 342 and the second tube 346 each define internal suture passageways (not shown or labeled) through which the respective sutures 332 and 336 can be threaded through. The trochanter gripper 340 and specifically the first tube 342, the second tube 346, and the connector 348 provide increased engagement surface areas for engagement with the medial interior portion 52, the superior portion 60, and the lateral portion 56 of the trochanter 50. It should also be noted that the connecter 348 is positioned such that it does not interfere with the muscle 70. In other words, the tubes 342 and 346 and the connector 348 define a space for the muscles 70 and specifically the abductor muscles.

Additionally, the trochanter gripper 340 includes a plurality of teeth configured to engage the trochanter 50. Specifically, the first tube 342 includes teeth 343 and 345 and the second tube 346 includes teeth 347 and 349. The teeth 343 and 347 are configured to engage the medial interior portion 52 of the trochanter 50. The teeth 345 and 349 are configured to engage the lateral portion 56 of the trochanter 50. These teeth 343, 345, 347, and 349 provide further increased engagement with the anterior portion 52 and the posterior portion 56 of the trochanter 50.

Similar to the above described first embodiment, the first section 332a of the first suture 332 and the first section 336a of the second suture 336 are respective end sections and are securely attached to the implant connector as described above.

The second section of the first suture 332 and the second section of the second suture 336 are respective intermediate sections and are configured to extend through respective anterior portions of the first tube 342 and the second tube 346 of the trochanter gripper 340.

The third section of the first suture 332 and the third section of the second suture 336 are respective intermediate sections and are configured extend through respective top portions the first tube 342 and the second tube 346 of the trochanter gripper 340.

The fourth section of the first suture 332 and the fourth section of the second suture 336 are respective intermediate sections and are configured to extend through respective posterior portions of the trochanter gripper 340.

Similar to the above described first embodiment, the fifth section 332e of the first suture 332 and the fifth section 336e of the second suture 336 are respective intermediate sections and are configured to extend downwardly toward the trochanter engager securer 370.

Similar to the above described first embodiment, the sixth section 332f of the first suture 332 and the sixth section 336f of the second suture 336 are respective end sections and are securely attached to the trochanter engager securer 370. Like the above embodiment, in this example embodiment, the sixth section 332f of the first suture 332 and the sixth section 336f of the second suture 336 extend through the openings in the trochanter engager securer 370 and are securely attached thereto.

The first section 332a of the first suture 332, the first section 336a of the second suture 336, the fifth section 332e of the first suture 332, the fifth section 336e of the second suture 336, the sixth section 332f of the first suture 332, and the sixth section 336f of the second suture 336 collectively function to maintain the second section of the first suture 332, the second section of the second suture 336, the third section of the first suture 332, the third section of the second suture 336, the fourth section of the first suture 332, and the fourth section of the second suture 336 in the first tube 342 and the second tube 346 of the trochanter gripper 340 and to in combination with the teeth 343, 345, 347, and 349 limit movement of the trochanter gripper 370 with respect to the trochanter 50. Accordingly, the second section of the first suture 332, the second section of the second suture 336, the third section of the first suture 332, the third section of the second suture 336, the fourth section of the first suture 332, and the fourth section of the second suture 336 collectively function to respectively cause the first tube 342 and the second tube 346 of the trochanter gripper 340 to engage the various portions of the trochanter 50 to: (a) provide support for the trochanter 50; (b) provide a link between the implant 80 and various distal points of the trochanter 50 to repair muscle or bone attachments; (d) provide oppose deforming forces to the soft tissue attachments of any fractured portion of the trochanter 50; (e) restore anatomic configuration of the trochanter 50; and (f) maintain a mechanical environment to facilitate healing of the trochanter 50. In this example embodiment, the first suture 332 and the second suture 336 are each made from braided polyester; however, it should be appreciated that the first suture 332 and the second suture 336 can each be made from other suitable materials such as, for example a metallic cable, in accordance with the present disclosure. It should also be appreciated that: (1) the first suture 332 and the second suture 336 can be otherwise suitably configured and sized in accordance with the present disclosure; (2) the first suture 332 and the second suture 336 are identical in this example embodiment but can be different in accordance with the present disclosure; (3) the quantity of sutures can vary in accordance with the present disclosure; and (4) the quantity of sections of the sutures and the specific functions of those sections of the sutures can vary in accordance with the present disclosure.

In this example embodiment, the trochanter gripper 340 is made from titanium alloys; however, it should be appreciated that the trochanter gripper 340 can be made from other suitable materials in accordance with the present disclosure. It should also be appreciated that: (1) the trochanter gripper 340 can be otherwise suitably configured and sized in accordance with the present disclosure; (2) the quantity of tubes of the trochanter gripper 340 can be vary in accordance with the present disclosure; (3) the quantity of sutures configured to engage the trochanter gripper 340 can vary in accordance with the present disclosure; (4) the engagement of the sutures with the trochanter gripper 340 can vary in accordance with the present disclosure; and (5) the quantity of teeth can vary in accordance with the present disclosure.

In this example embodiment, the trochanter engager securer 370 includes: (1) suture receiver 372; (2) a first cable receiver 376; (3) a second cable receiver 380; and (4) a cable 384. The trochanter engager securer 370 in this example embodiment is identical to the trochanter engager securer 170 explained above and is thus not described again for brevity.

It should be appreciated that the positions of the suture receiver 372 and the first cable receiver 376 can be switched (such as shown in FIGS. 22, 23, 24, and 25) to bring the sutures closer to the posterior side of the femur (including the trochanter). It should also be appreciated that one end of the cable 384 can have a bead (such as shown in FIG. 21) for engagement with the second cable receiver 380. It should also be appreciated that the second cable receiver 380 can be alternatively positioned such as on the opposite side of the femur (such as shown in FIGS. 22, 23, 24, and 25). It should further be appreciated that the trochanter engager securer 370 can be positioned closer to the trochanter (such as shown in FIGS. 22, 23, 24, and 25) to bring the sutures closer to the posterior side of the femur (including the trochanter).

In this example embodiment, the trochanter engager securer 370 is made from stainless steel multifilament cable; however, it should be appreciated that the trochanter engager securer 370 can be made from other suitable materials in accordance with the present disclosure. It should also be appreciated that the trochanter engager securer 370 can be otherwise suitably configured and sized in accordance with the present disclosure.

FIGS. 5 and 6 show the trochanter securement apparatus 300 after this apparatus 300 has be secured to the femur 10 and to the implant 80 that is inserted in the femur 10. More specifically, FIGS. 5 and 6 show the apparatus 300 after the implant connector 310 has been securely connected to the implant 80, after the trochanter engager 330 including the trochanter gripper 340 has been positioned to engage the trochanter 30 of the femur 10, after the trochanter engager securer 370 has been attached to an intermediate portion 20 of the femur 10 below the trochanter 50, and after the trochanter engager 330 has been securely connected to the trochanter engager securer 370. This example embodiment can be employed for smaller or more significant fractures or to prevent fractures, where the sutures 332 and 336 (or alternatively cables) and the trochanter gripper 340 function together on the trochanter. This example embodiment is also easy to install and use, and can be seated in various different positions. This example embodiment is also relatively simple and inexpensive to manufacture. It should also be appreciated that the trochanter engager securer can function as a distal anchoring point through which tension is maintained upon the more proximal trochanter engager and sutures/cable.

Figure 7:
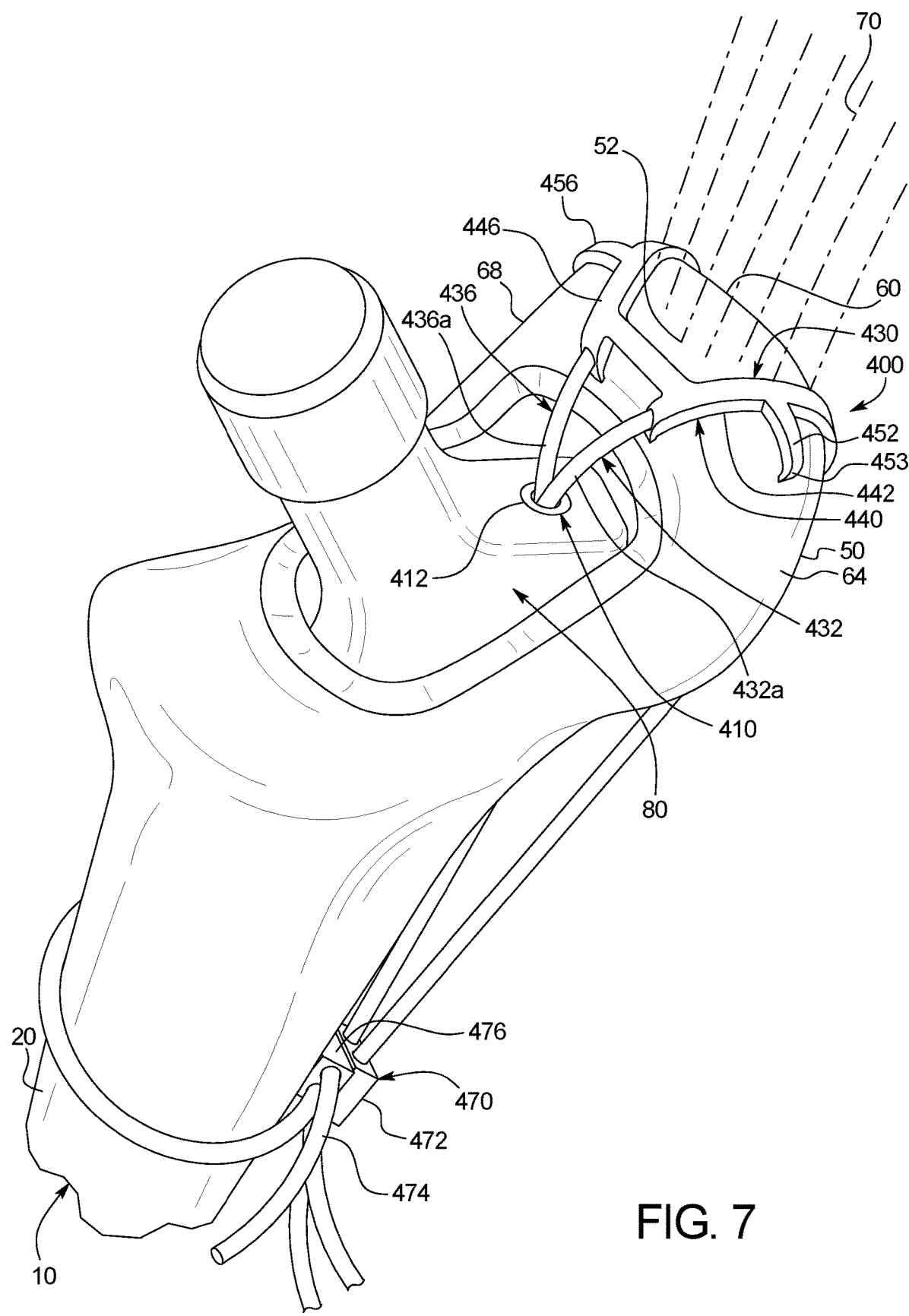
FIG. 7 is a fragmentary anterolateral perspective view of an upper portion of a femur (including the trochanter), a portion of part of an implant shown inserted into the femur, and a trochanter securement apparatus of another example embodiment of the present disclosure, and showing this example trochanter securement apparatus secured to the implant and secured to the femur.
Figure 8:
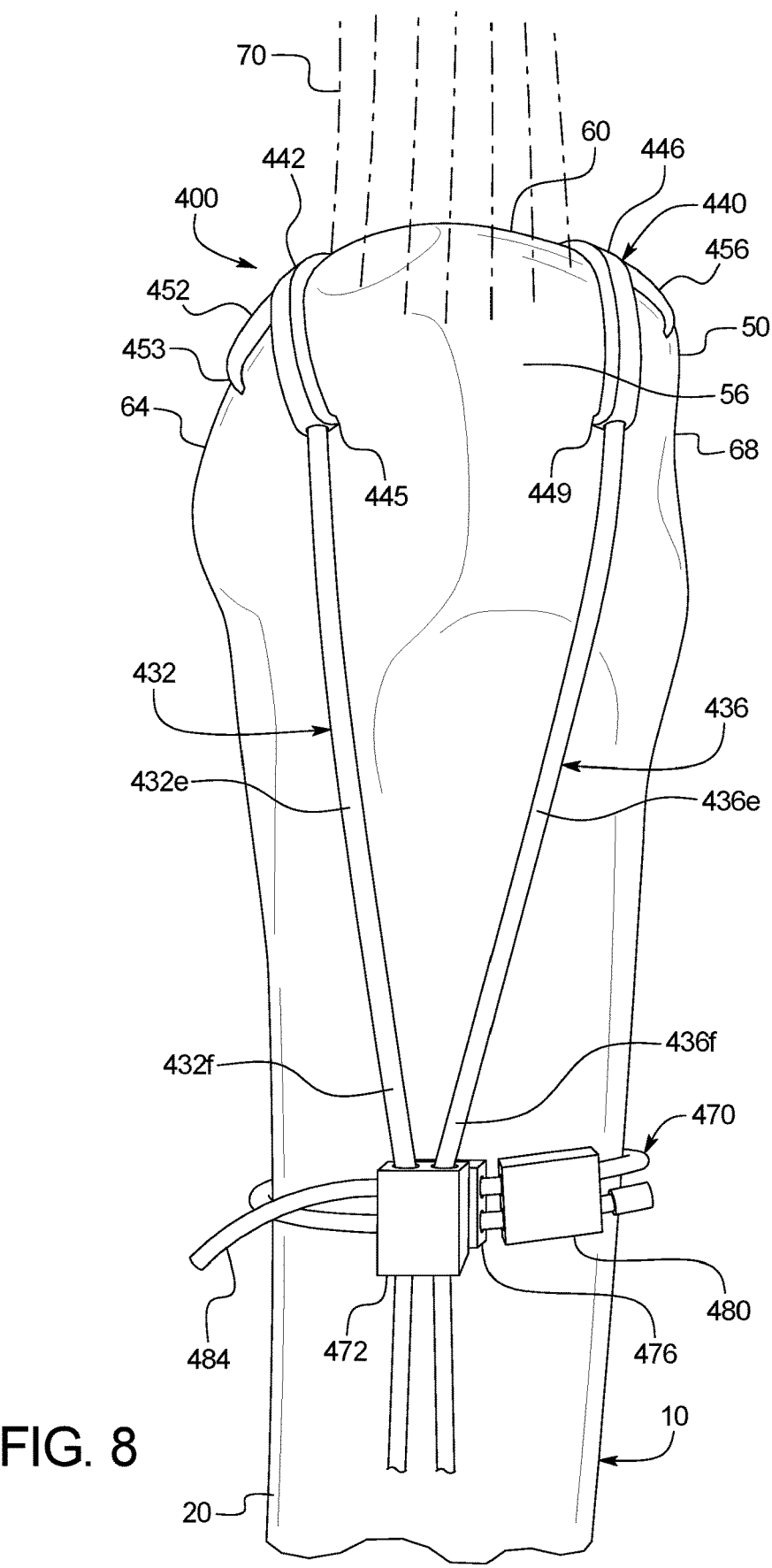
FIG. 8 is a fragmentary lateral perspective view of the upper portion of the femur (including the trochanter) of FIG. 7 and the trochanter securement apparatus of FIG. 7, and showing this example trochanter securement apparatus secured to the femur.

FIGS. 7 and 8 illustrate another example embodiment of a direct anterior hip replacement trochanter securement apparatus of the present disclosure. This example direct anterior hip replacement trochanter securement apparatus is generally indicated by numeral 400, and is referred to herein for brevity as the trochanter securement apparatus 400 or the apparatus 400. This example trochanter securement apparatus 400 generally includes: (1) an implant connector 410; (2) a trochanter engager 430; and (3) a trochanter engager securer 470.

More specifically, in this example embodiment, the implant connector 410 includes a fastener 412 removably connectable to the implant 80. The fastener 410 in this example embodiment is identical to the fastener 110 explained above and is thus not described again for brevity. In this example embodiment, the fastener 412 is made from a titanium alloy; however, it should be appreciated that the fastener 412 can be made from other suitable materials in accordance with the present disclosure. It should also be appreciated that the fastener can be otherwise suitably configured and sized in accordance with the present disclosure.

In this example embodiment, the trochanter engager 430 includes a first suture 432, a second suture 436, and a trochanter gripper 440. The first suture 432 and the second suture 436 are configured to extend through the trochanter gripper 440 and to hold the trochanter engager 430 in place.

The first suture 432 and the second suture 436 are both elongated flat flexible members. The first suture 432 includes: (a) a first section 432a; (b) a second section (not shown); (c) a third section (not shown); (d) a fourth section (not shown); (e) a fifth section 432e; and (f) a sixth section 432f. Likewise, the second suture 436 includes: (a) a first section 436a; (b) a second section (not shown); (c) a third section (not shown); (d) a fourth section (not shown); (e) a fifth section 436e; and (f) a sixth section 436f.

In this example embodiment, the trochanter gripper 440 is configured to engage each of the medial interior portion 52, the superior portion 60, and the lateral portion 56 of the trochanter 50. The trochanter gripper 440 includes a first tube 442, a second tube 446, and a connector 448 that suitably connects the first tube 442 and the second tube 446. The first tube 442 and the second tube 446 each define internal suture passageways (not shown or labeled) through which the respective sutures 432 and 436 can be threaded through. It should also be noted that the connecter 448 is positioned such that it does not interfere with the muscle 70. In other words, the tubes 442 and 446 and the connector 448 define a space for the muscles 70 and specifically the abductor muscles. The trochanter gripper 440 and specifically the first tube 442, the second tube 446, and the connector 448 provide increased engagement with the medial interior portion 52, the superior portion 60, and the lateral portion 56 of the trochanter 50.

Additionally, the trochanter gripper 440 includes a plurality of teeth configured to engage the trochanter 50. Specifically, the first tube 442 includes teeth 443 and 445 and the second tube 446 includes teeth 447 and 449. The teeth 443 and 447 are configured to engage the medial interior portion 52 of the trochanter 50. The teeth 447 and 449 are configured to engage the lateral portion 56 of the trochanter 50. These teeth 443, 445, 447, and 449 provide further increased engagement with the anterior portion 52 and the posterior portion 56 of the trochanter 50.

Additionally, the trochanter gripper 440 includes a plurality of outwardly extending engagement arms 452 and 456 configured to engage the trochanter 50. Arm 452 is connected to and extends outwardly from tube 442 and arm 456 is connected to and extends outwardly from tube 446. The first arm 452 includes tooth 453 and the second arm 456 includes tooth 457 (not shown). The tooth 453 is configured to engage the portion 64 of the trochanter 50. It should be appreciated that this may be the anterior or posterior portion depending on whether it is for the right or left hip. The tooth 457 is configured to engage the portion 68 of the trochanter 50. It should be appreciated that this may be the anterior or posterior portion depending on whether it is for the right or left hip. These teeth 453 and 457 provide further increased engagement with the trochanter 50. It should be appreciated that any of the teeth can be in the form of a hook or any other suitable form.

Similar to the above described first embodiment, the first section 432a of the first suture 432 and the first section 436a of the second suture 436 are respective end sections and are securely attached to the implant connector as described above.

The second section of the first suture 432 and the second section of the second suture 436 are respective intermediate sections and are configured to extend through respective anterior portions of the first tube 442 and the second tube 446 of the trochanter gripper 440.

The third section of the first suture 432 and the third section of the second suture 436 are respective intermediate sections and are configured extend through respective top portions the first tube 442 and the second tube 446 of the trochanter gripper 440.

The fourth section of the first suture 432 and the fourth section of the second suture 436 are respective intermediate sections and are configured to extend through respective posterior portions of the trochanter gripper 440.

Similar to the above described first embodiment, the fifth section 432e of the first suture 432 and the fifth section 436e of the second suture 436 are respective intermediate sections and are configured to extend downwardly toward the trochanter engager securer 470.

Similar to the above described first embodiment, the sixth section 432f of the first suture 432 and the sixth section 436f of the second suture 436 are respective end sections and are securely attached to the trochanter engager securer 470. Like the above embodiment, in this example embodiment, the sixth section 432f of the first suture 432 and the sixth section 436f of the second suture 436 extend through the openings in the trochanter engager securer 470 and are securely attached thereto.

The first section 432a of the first suture 332, the first section 436a of the second suture 436, the fifth section 432e of the first suture 432, the fifth section 436e of the second suture 436, the sixth section 432f of the first suture 432, and the sixth section 436f of the second suture 436 collectively function to maintain the second section of the first suture 432, the second section of the second suture 436, the third section of the first suture 432, the third section of the second suture 436, the fourth section of the first suture 432, and the fourth section of the second suture 436 in the first tube 442 and the second tube 446 of the trochanter gripper 440 and to in combination with the teeth 443, 445, 447, 449, 453, and 457 limit movement of the trochanter gripper 370 with respect to the trochanter 50. Accordingly, the second section of the first suture 432, the second section of the second suture 436, the third section of the first suture 432, the third section of the second suture 436, the fourth section of the first suture 432, and the fourth section of the second suture 436 collectively function to respectively cause the first tube 442 and the second tube 446 of the trochanter gripper 440 to engage the various portions of the trochanter 50 to: (a) provide support for the trochanter 50; (b) provide a link between the implant 80 and various distal points of the trochanter 50 to repair muscle or bone attachments; (d) provide oppose deforming forces to the soft tissue attachments of any fractured portion of the trochanter 50; (e) restore anatomic configuration of the trochanter 50; and (f) maintain a mechanical environment to facilitate healing of the trochanter 50.

In this example embodiment, the first suture 432 and the second suture 436 are each made from braided polyester; however, it should be appreciated that the first suture 432 and the second suture 436 can be made from other suitable materials such as, for example stainless steel multifilament cable or braided Kevlar cable, in accordance with the present disclosure. It should also be appreciated that: (1) the first suture 432 and the second suture 436 can be otherwise suitably configured and sized in accordance with the present disclosure; (2) the first suture 432 and the second suture 436 are identical in this example embodiment but can be different in accordance with the present disclosure; (3) the quantity of sutures can vary in accordance with the present disclosure; and (4) the quantity of sections of the sutures and the specific functions of those sections of the sutures can vary in accordance with the present disclosure.

In this example embodiment, the trochanter gripper 440 is made from titanium alloys; however, it should be appreciated that the trochanter gripper 440 can be made from other suitable materials in accordance with the present disclosure. It should also be appreciated that: (1) the trochanter gripper 440 can be otherwise suitably configured and sized in accordance with the present disclosure; (2) the quantity of tubes of the trochanter gripper 440 can be vary in accordance with the present disclosure; (3) the quantity of sutures configured to engage the trochanter gripper 440 can vary in accordance with the present disclosure; (4) the engagement of the sutures with the trochanter gripper 440 may vary in accordance with the present disclosure; (5) the quantity of teeth may vary in accordance with the present disclosure; and (6) the quantity of arms may vary in accordance with the present disclosure.

In this example embodiment, the trochanter engager securer 470 includes: (1) suture/cable receiver 472; (2) a first cable receiver 476; (3) a second cable receiver 480; and (4) a cable 484. The trochanter engager securer 470 in this example embodiment is identical to the trochanter engager securer 170 explained above and is thus not described again for brevity.

It should be appreciated that the positions of the suture receiver 472 and the first cable receiver 476 can be switched (such as shown in FIGS. 22, 23, 24, and 25) to bring the sutures closer to the posterior side of the femur (including the trochanter). It should also be appreciated that one end of the cable 484 can have a bead (such as shown in FIG. 21) for engagement with the second cable receiver 480. It should also be appreciated that the second cable receiver 480 can be alternatively positioned such as on the opposite side of the femur (such as shown in FIGS. 22, 23, 24, and 25). It should further be appreciated that the trochanter engager securer 470 can be positioned closer to the trochanter (such as shown in FIGS. 22, 23, 24, and 25) to bring the sutures closer to the posterior side of the femur (including the trochanter).

In this example embodiment, the trochanter engager securer 470 is made from a stainless steel alloy; however, it should be appreciated that the trochanter engager securer 470 can be made from other suitable materials in accordance with the present disclosure. It should also be appreciated that the trochanter engager securer 470 can be otherwise suitably configured and sized in accordance with the present disclosure.

FIGS. 7 and 8 show the trochanter securement apparatus 400 after this apparatus 400 has be secured to the femur 10 and to the implant 80 that is inserted in the femur 10. More specifically, FIGS. 7 and 8 show the apparatus 400 after the implant connector 410 has been securely connected to the implant 80, after the trochanter engager 430 has been positioned to engage the trochanter 30 of the femur 10, after the trochanter engager securer 470 has been attached to an intermediate portion 20 of the femur 10 below the trochanter 50, and after the trochanter engager 430 has been securely connected to the trochanter engager securer 470. This example embodiment may be employed for smaller or more significant fractures or to prevent fractures, where the sutures 432 and 436 (or alternatively cables) and the trochanter gripper 440 function together on the trochanter. This example embodiment is also easy to install and use, and can be seated in various different positions. This example embodiment is also relatively simple and inexpensive to manufacture. It should also be appreciated that the trochanter engager securer may function as a distal anchoring point through which tension is maintained upon the more proximal trochanter engager and sutures/cable. It should also be appreciated that this example embodiment is configured to prevent anterior or posterior trochanteric migration with the additional anterior and posterior teeth such as hook shaped teeth. Similarly, it can also engage smaller anterior or posterior fragments.

Figure 9:
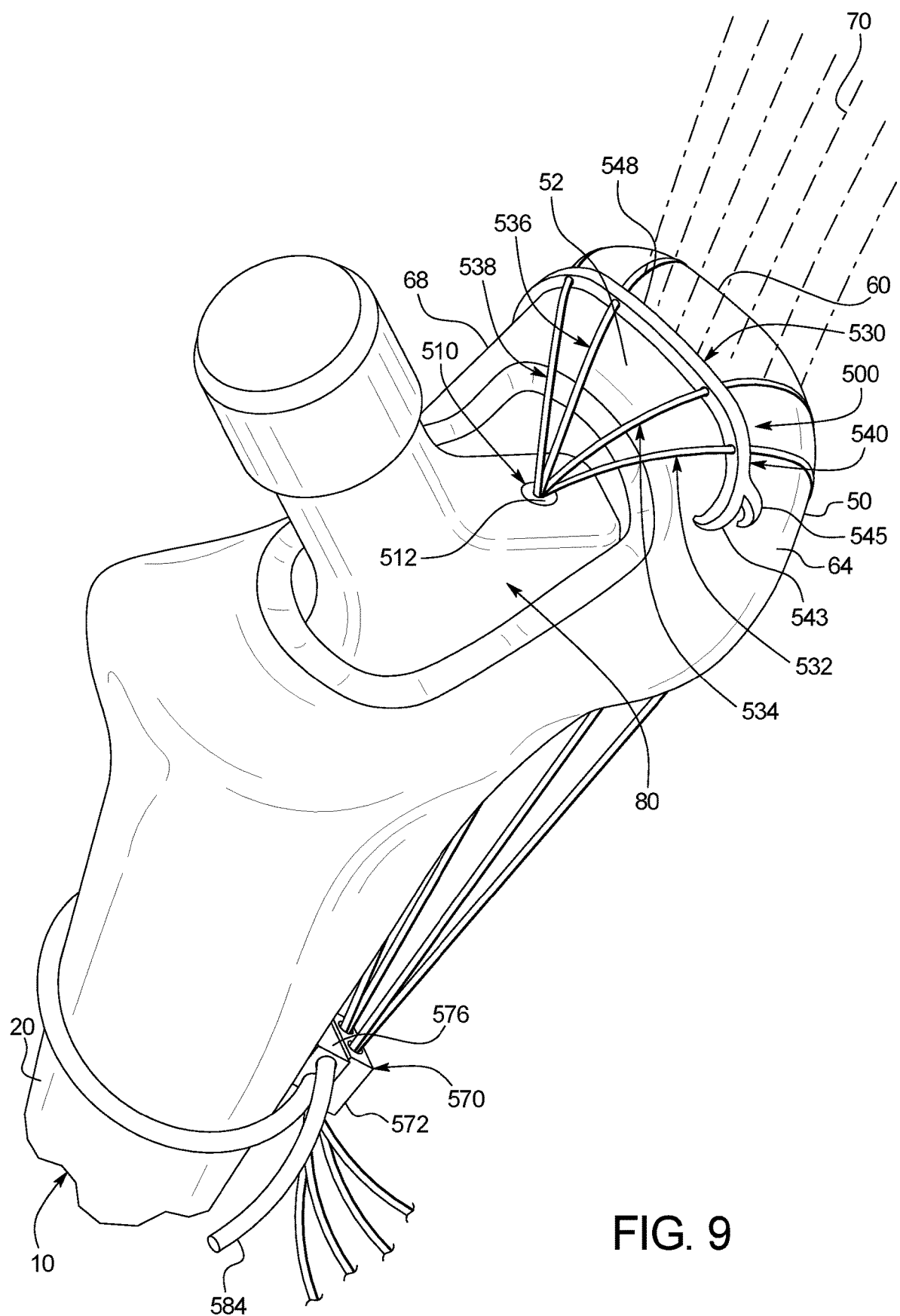
FIG. 9 is a fragmentary anterolateral perspective view of an upper portion of a femur (including the trochanter), a portion of part of an implant shown inserted into the femur, and a trochanter securement apparatus of another example embodiment of the present disclosure, and showing this example trochanter securement apparatus secured to the implant and secured to the femur.
Figure 10:
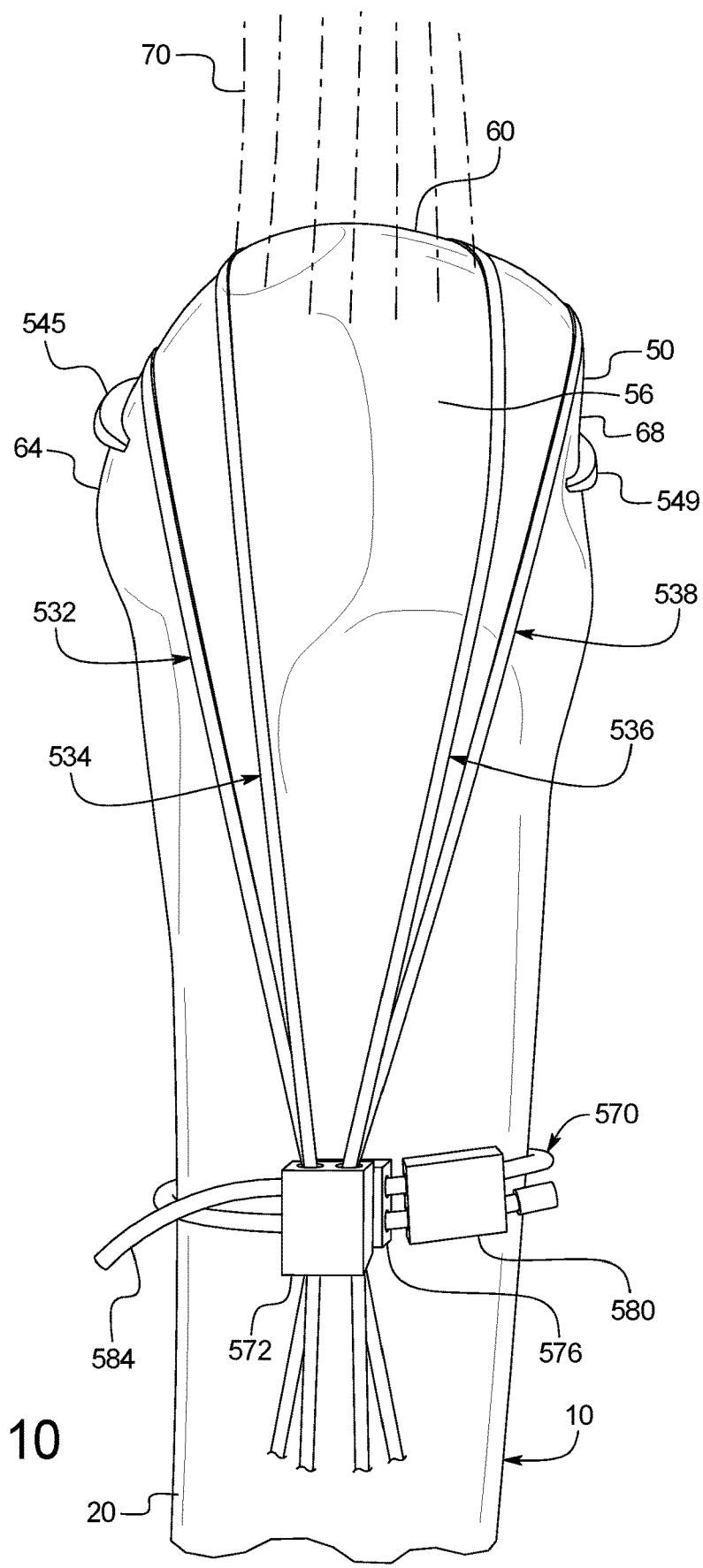
FIG. 10 is a fragmentary lateral perspective view of the upper portion of the femur (including the trochanter) of FIG. 9 and the trochanter securement apparatus of FIG. 9, and showing this example trochanter securement apparatus secured to the femur.

FIGS. 9 and 10 illustrate another example embodiment of a direct anterior hip replacement trochanter securement apparatus of the present disclosure. This example direct anterior hip replacement trochanter securement apparatus is generally indicated by numeral 500, and is referred to herein for brevity as the trochanter securement apparatus 500 or the apparatus 500. This example trochanter securement apparatus 500 generally includes: (1) an implant connector 510; (2) a trochanter engager 530; and (3) a trochanter engager securer 570.

More specifically, in this example embodiment, the implant connector 510 includes a fastener 512 removably connectable to the implant 80. The fastener 510 in this example embodiment is identical to the fastener 110 explained above and is thus not described again for brevity. In this example embodiment, the fastener 512 is made from a titanium alloy however, it should be appreciated that the fastener 512 can be made from other suitable materials in accordance with the present disclosure. It should also be appreciated that the fastener can be otherwise suitably configured and sized in accordance with the present disclosure.

In this example embodiment, the trochanter engager 530 includes a first suture 532, a second suture 534, a third suture 536, a fourth suture 538, and a trochanter gripper 540. The first suture 532, the second suture 534, the third suture 536, and the fourth suture 538 are configured to extend through the trochanter gripper 540 and to hold the trochanter engager 530 in place.

The first suture 532, the second suture 534, the third suture 536, and the fourth suture 538 are each elongated flat flexible members. Similar to the above embodiments, each of the first suture 532, the second suture 534, the third suture 536, and the fourth suture 538 includes: (a) a first section (not labeled); (b) a second section (not labeled); (c) a third section (not labeled); (d) a fourth section (not labeled); (e) a fifth section (not labeled); and (f) a sixth section (not labeled).

Similar to the above described first embodiment, each of the respective first sections of the first suture 532, the second suture 534, the third suture 536, and the fourth suture 538 are respective end sections and are securely attached to the fastener 512.

Similar to the above described first embodiment, each of the respective second sections of the first suture 532, the second suture 534, the third suture 536, and the fourth suture 538 are respective intermediate sections and are configured to partially engage the medial interior portion 52 of the trochanter 50 and to extend through the trochanter gripper.

Similar to the above described first embodiment, each of the respective first sections of the first suture 532, the second suture 534, the third suture 536, and the fourth suture 538 are respective intermediate sections and are configured to engage the superior portion 60 of the trochanter 50.

Similar to the above described first embodiment, each of the respective first sections of the first suture 532, the second suture 534, the third suture 536, and the fourth suture 538 are respective intermediate sections and are configured to engage the lateral portion 56 of the trochanter 50.

Similar to the above described first embodiment, each of the respective first sections of the first suture 532, the second suture 534, the third suture 536, and the fourth suture 538 are respective intermediate sections and are configured to extend distally toward the trochanter engager securer 570.

Similar to the above described first embodiment, each of the respective first sections of the first suture 532, the second suture 534, the third suture 536, and the fourth suture 538 are respective end sections and are securely attached to the trochanter engager securer 570. Specifically, in this example embodiment, the sixth section of each of the respective first sections of the first suture 532, the second suture 534, the third suture 536, and the fourth suture 538 extends through the openings in the trochanter engager securer 570 and are securely attached thereto.

In this example embodiment, the trochanter gripper 540 is configured to engage each of the medial interior portion 52, the first side portion 64, and the second side portion 68 of the trochanter 50. The trochanter gripper 540 includes a connector 548 that defines four internal suture passageways (labeled) through which the respective sutures 532, 534, 536, and 538 can be threaded through. The trochanter gripper 540 and specifically the connector 548 in configured to engage the anterior portion 52 of the trochanter 50.

Additionally, the trochanter gripper 540 includes a plurality of teeth configured to engage the trochanter 50. Specifically, the connector 548 includes teeth 543, 545, 547, and 549. The teeth 543 and 545 are configured to engage the first side portion 64 of the trochanter 50. The teeth 547 and 549 are configured to engage the second side portion 68 of the trochanter 50. These teeth 543, 545, 547, and 549 provide further increased engagement with the trochanter 50. It should be appreciated that the connector 548 may be wider to encompass more of the bone. In one sense, the connector 548 functions as two outwardly extending engagement arms configured to engage the trochanter 50.

Accordingly, each of the first suture 532, the second suture 534, the third suture 536, and the fourth suture 538 collectively function to respectively cause the connector 548 and the teeth 543, 545, 547, and 549 to engage the various portions of the trochanter 50 to: (a) provide support for the trochanter 50; (b) provide a link between the implant 80 and various distal points of the trochanter 50 to repair muscle or bone attachments; (d) provide oppose deforming forces to the soft tissue attachments of any fractured portion of the trochanter 50; (e) restore anatomic configuration of the trochanter 50; and (f) maintain a mechanical environment to facilitate healing of the trochanter 50.

In this example embodiment, each of the first suture 532, the second suture 534, the third suture 536, and the fourth suture 538 are made from braided polyester; however, it should be appreciated that each of the first suture 532, the second suture 534, the third suture 536, and the fourth suture 538 can be made from other suitable materials in accordance with the present disclosure. It should also be appreciated that: (1) each of the first suture 532, the second suture 534, the third suture 536, and the fourth suture 538 can be otherwise suitably configured and sized in accordance with the present disclosure; (2) each of the first suture 532, the second suture 534, the third suture 536, and the fourth suture 538 are identical in this example embodiment but can be different in accordance with the present disclosure; (3) the quantity of sutures may vary in accordance with the present disclosure; and (4) the quantity of sections of the sutures and the specific functions of those sections of the sutures may vary in accordance with the present disclosure.

In this example embodiment, the trochanter gripper 540 is made from titanium alloys; however, it should be appreciated that the trochanter gripper 540 can be made from other suitable materials in accordance with the present disclosure. It should also be appreciated that: (1) the trochanter gripper 540 can be otherwise suitably configured and sized in accordance with the present disclosure; (2) the quantity of connectors of the trochanter gripper 540 can be vary in accordance with the present disclosure; (3) the quantity of sutures configured to engage the trochanter gripper 540 can vary in accordance with the present disclosure; (4) the engagement of the sutures with the trochanter gripper 540 may vary in accordance with the present disclosure; and (5) the quantity of teeth may vary in accordance with the present disclosure.

In this example embodiment, the trochanter engager securer 570 includes: (1) suture receiver 572; (2) a first cable receiver 576; (3) a second cable receiver 580; and (4) a cable 584. The trochanter engager securer 570 in this example embodiment is identical to the trochanter engager securer 170 explained above and is thus not described again for brevity.

It should be appreciated that the positions of the suture receiver 572 and the first cable receiver 576 can be switched (such as shown in FIGS. 22, 23, 24, and 25) to bring the sutures closer to the posterior side of the femur (including the trochanter). It should also be appreciated that one end of the cable 584 can have a bead (such as shown in FIG. 21) for engagement with the second cable receiver 550. It should also be appreciated that the second cable receiver 280 can be alternatively positioned such as on the opposite side of the femur (such as shown in FIGS. 22, 23, 24, and 25). It should further be appreciated that the trochanter engager securer 570 can be positioned closer to the trochanter (such as shown in FIGS. 22, 23, 24, and 25) to bring the sutures closer to the posterior side of the femur (including the trochanter).

In this example embodiment, the trochanter engager securer 570 is made from titanium alloys; however, it should be appreciated that the trochanter engager securer 570 can be made from other suitable materials in accordance with the present disclosure. It should also be appreciated that the trochanter engager securer 570 can be otherwise suitably configured and sized in accordance with the present disclosure.

FIGS. 9 and 10 show the trochanter securement apparatus 500 after this apparatus 500 has be secured to the femur 10 and to the implant 80 that is inserted in the femur 10. More specifically, FIGS. 9 and 10 show the apparatus 500 after the implant connector 510 has been securely connected to the implant 80, after the trochanter engager 530 has been positioned to engage the trochanter 30 of the femur 10, after the trochanter engager securer 570 has been attached to an intermediate portion 20 of the femur 10 below the trochanter 50, and after the trochanter engager 530 has been securely connected to the trochanter engager securer 570. This example embodiment may be employed for smaller or more significant fractures or to prevent fractures, where the sutures 532, 534, 536, and 538 (or alternatively cables) and the trochanter gripper 540 function together on the trochanter. This example embodiment is also easy to install and use, and can be seated in various different positions. This example embodiment is also relatively simple and inexpensive to manufacture. It should also be appreciated that this example embodiment is configured to prevent anterior or posterior trochanteric migration with the additional anterior and posterior teeth. Similarly, it can also engage smaller anterior or posterior fragments. Thus, this example embodiment may be particularly suited for addressing multiple types of fractures.

Figure 11:
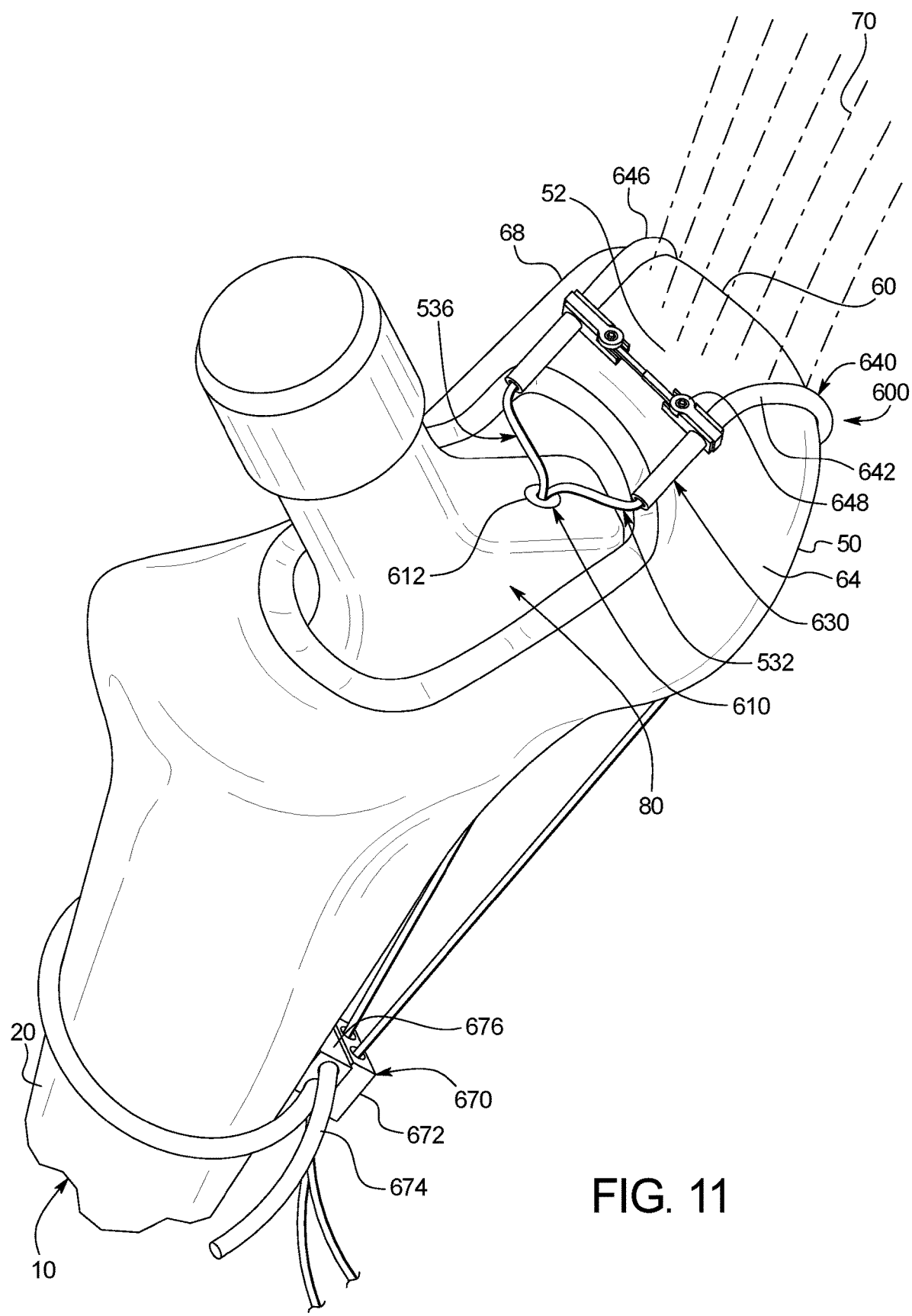
FIG. 11 is a fragmentary anterolateral perspective view of an upper portion of a femur (including the trochanter), a portion of part of an implant shown inserted into the femur, and a trochanter securement apparatus of another example embodiment of the present disclosure, and showing this example trochanter securement apparatus secured to the implant and secured to the femur.
Figure 12:
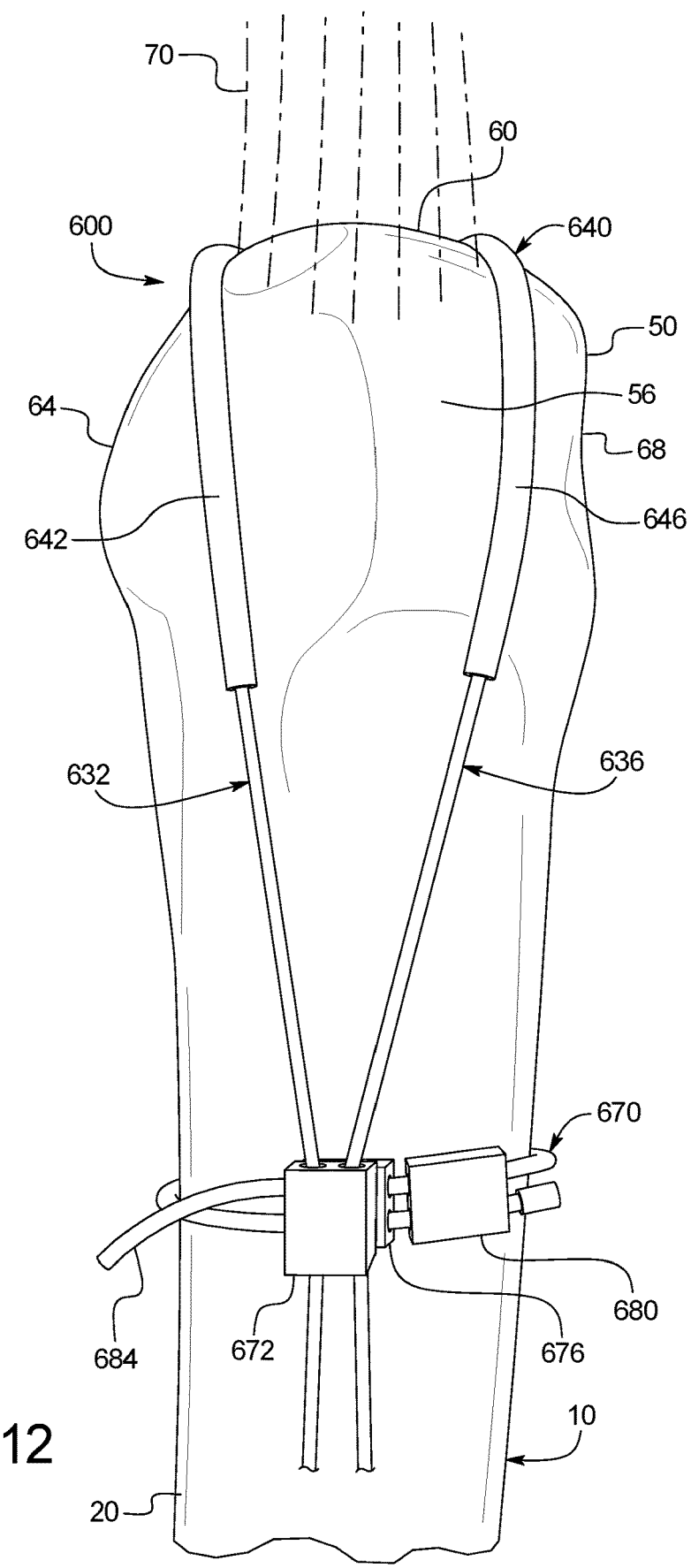
FIG. 12 is a fragmentary lateral perspective view of the upper portion of the femur (including the trochanter) of FIG. 11 and the trochanter securement apparatus of FIG. 11, and showing this example trochanter securement apparatus secured to the femur.

FIGS. 11 and 12 illustrate another example embodiment of a direct anterior hip replacement trochanter securement apparatus of the present disclosure. This example direct anterior hip replacement trochanter securement apparatus is generally indicated by numeral 600, and is referred to herein for brevity as the trochanter securement apparatus 600 or the apparatus 600. This example trochanter securement apparatus 600 generally includes: (1) an implant connector 610; (2) a trochanter engager 630; and (3) a trochanter engager securer 670.

More specifically, in this example embodiment, the implant connector 610 includes a fastener 612 removably connectable to the implant 80. The fastener 610 in this example embodiment is identical to the fastener 110 explained above and is thus not described again for brevity. In this example embodiment, the fastener 612 is made from a titanium alloy; however, it should be appreciated that the fastener 612 can be made from other suitable materials in accordance with the present disclosure. It should also be appreciated that the fastener can be otherwise suitably configured and sized in accordance with the present disclosure.

In this example embodiment, the trochanter engager 630 includes a first suture 632, a second suture 636, and a trochanter gripper 640. The first suture 632 and the second suture 636 are configured to extend through the trochanter gripper 640 and to hold the trochanter engager 630 in place.

Similar to the second embodiment described above, the first suture 632 and the second suture 636 are both elongated flat flexible members. Since the first suture 632 and the second suture 636 are identical to the first suture 232 and the second suture 236 described above, for brevity, these are not described again in detail herein.

In this example embodiment, the trochanter gripper 640 is configured to engage each of the anterior portion 52, the top portion 60, and the posterior portion 56 of the trochanter 50. The trochanter gripper 640 includes a first tube 642, a second tube 646, and an adjustable connector 648 that is configured to suitably connect the first tube 642 and the second tube 646 at different spaced apart distances. The first tube 642 and the second tube 646 each define internal suture passageways (not shown or labeled) through which the respective sutures 632 and 636 can be threaded through. The adjustable connector 648 may be any suitable connecter that is configured such that the surgeon can position the first tube 642 and the second tube 646 at any one of a plurality of different distances from each other. The trochanter gripper 640 and specifically the first tube 642, the second tube 646, and the connector 648 provide increased engagement surface areas for engagement with the anterior portion 52, the top portion 60, and the posterior portion 56 of the trochanter 50.

The first suture 632 and the second suture 636 limit movement of the trochanter gripper 640 with respect to the trochanter 50. Accordingly, the first suture 632, the second suture 636, and the trochanter gripper 640 collectively function to respectively cause the first tube 642 and the second tube 646 of the trochanter gripper 640 to engage the various portions of the trochanter 50 to: (a) provide support for the trochanter 50; (b) provide a link between the implant 80 and various distal points of the trochanter 50 to repair muscle or bone attachments; (d) provide oppose deforming forces to the soft tissue attachments of any fractured portion of the trochanter 50; (e) restore anatomic configuration of the trochanter 50; and (f) maintain a mechanical environment to facilitate healing of the trochanter 50.

In this example embodiment, the first suture 632 and the second suture 636 are each made from braided polyester; however, it should be appreciated that the first suture 632 and the second suture 636 can be made from other suitable materials in accordance with the present disclosure. It should also be appreciated that: (1) the first suture 632 and the second suture 636 can be otherwise suitably configured and sized in accordance with the present disclosure; (2) the first suture 632 and the second suture 636 are identical in this example embodiment but can be different in accordance with the present disclosure; (3) the quantity of sutures may vary in accordance with the present disclosure; and (4) the quantity of sections of the sutures and the specific functions of those sections of the sutures may vary in accordance with the present disclosure.

In this example embodiment, the trochanter gripper 640 is made from titanium alloys; however, it should be appreciated that the trochanter gripper 640 can be made from other suitable materials in accordance with the present disclosure. It should also be appreciated that: (1) the trochanter gripper 640 can be otherwise suitably configured and sized in accordance with the present disclosure; (2) the quantity of tubes of the trochanter gripper 640 can be vary in accordance with the present disclosure; (3) the quantity of sutures configured to engage the trochanter gripper 640 can vary in accordance with the present disclosure; and (4) the engagement of the sutures with the trochanter gripper 640 may vary in accordance with the present disclosure.

In this example embodiment, the trochanter engager securer 670 includes: (1) suture receiver 672; (2) a first cable receiver 676; (3) a second cable receiver 680; and (4) a cable 684. The trochanter engager securer 670 in this example embodiment is identical to the trochanter engager securer 170 explained above and is thus not described again for brevity.

It should be appreciated that the positions of the suture receiver 672 and the first cable receiver 676 can be switched (such as shown in FIGS. 22, 23, 24, and 25) to bring the sutures closer to the posterior side of the femur (including the trochanter). It should also be appreciated that one end of the cable 684 can have a bead (such as shown in FIG. 21) for engagement with the second cable receiver 680. It should also be appreciated that the second cable receiver 680 can be alternatively positioned such as on the opposite side of the femur (such as shown in FIGS. 22, 23, 24, and 25). It should further be appreciated that the trochanter engager securer 670 can be positioned closer to the trochanter (such as shown in FIGS. 22, 23, 24, and 25) to bring the sutures closer to the posterior side of the femur (including the trochanter).

In this example embodiment, the trochanter engager securer 670 is made from titanium alloys; however, it should be appreciated that the trochanter engager securer 670 can be made from other suitable materials in accordance with the present disclosure. It should also be appreciated that the trochanter engager securer 670 can be otherwise suitably configured and sized in accordance with the present disclosure.

FIGS. 11 and 12 show the trochanter securement apparatus 600 after this apparatus 600 has be secured to the femur 10 and to the implant 80 that is inserted in the femur 10. More specifically, FIGS. 11 and 12 show the apparatus 600 after the implant connector 610 has been securely connected to the implant 80, after the trochanter engager 630 including the trochanter gripper 640 has been positioned to engage the trochanter 30 of the femur 10, after the trochanter engager securer 670 has been attached to an intermediate portion 20 of the femur 10 below the trochanter 50, and after the trochanter engager 630 has been securely connected to the trochanter engager securer 670. This example embodiment may be employed for smaller or more significant fractures or to prevent fractures, where the sutures 632 and 636 (or alternatively cables) and the trochanter gripper 640 function together on the trochanter. This example embodiment is also easy to install and use, and can be seated in various different positions. This example embodiment is also relatively simple and inexpensive to manufacture. It should also be appreciated that one advantage of this example embodiments is that enables on trochanter gripper 640 to be constructed and manufactured that fits trochanters of various dimensions.

Figure 13:
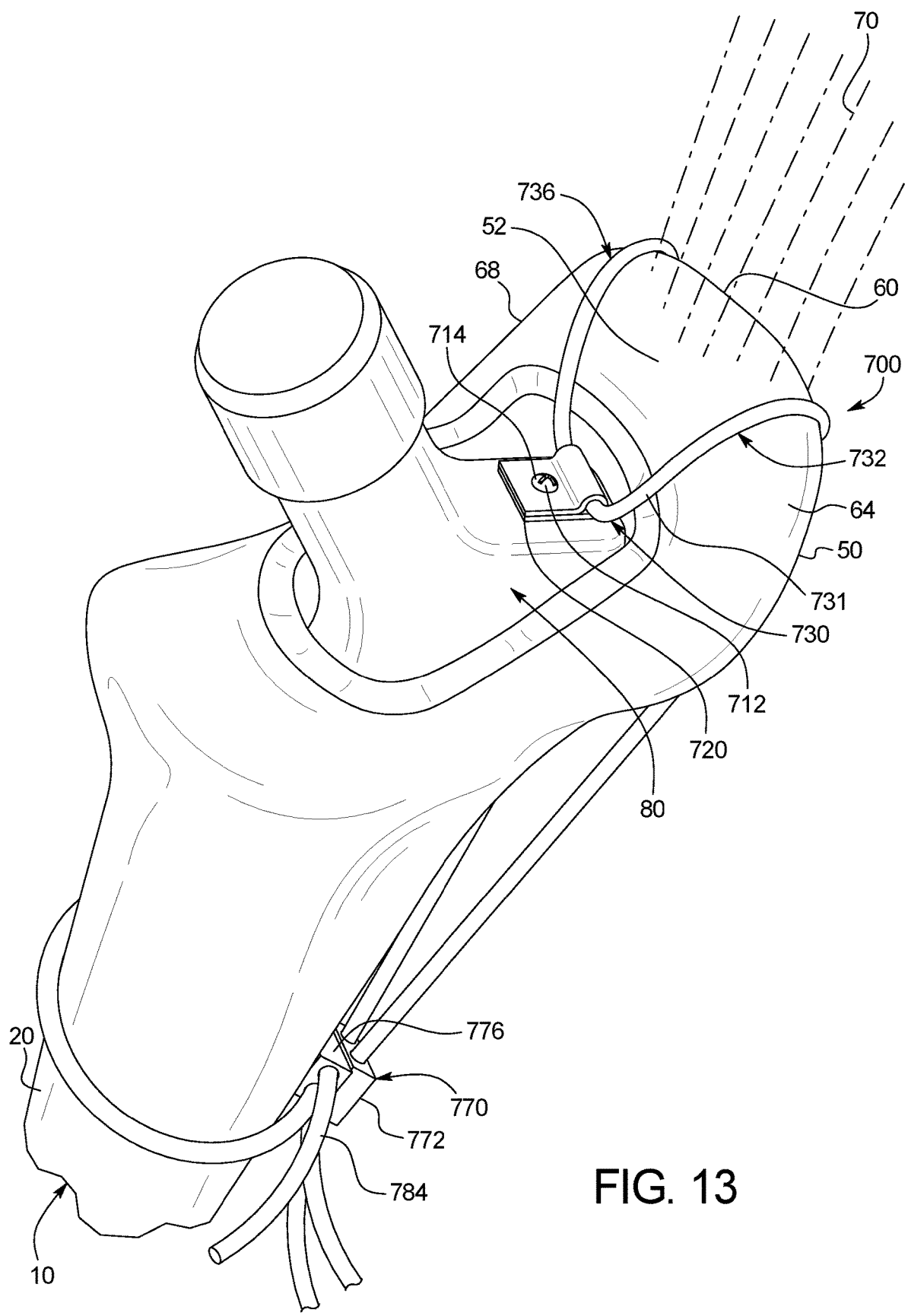
FIG. 13 is a fragmentary anterolateral perspective view of an upper portion of a femur (including the trochanter), a portion of part of an implant shown inserted into the femur, and a trochanter securement apparatus of another example embodiment of the present disclosure, and showing this example trochanter securement apparatus secured to the implant and secured to the femur.
Figure 14:
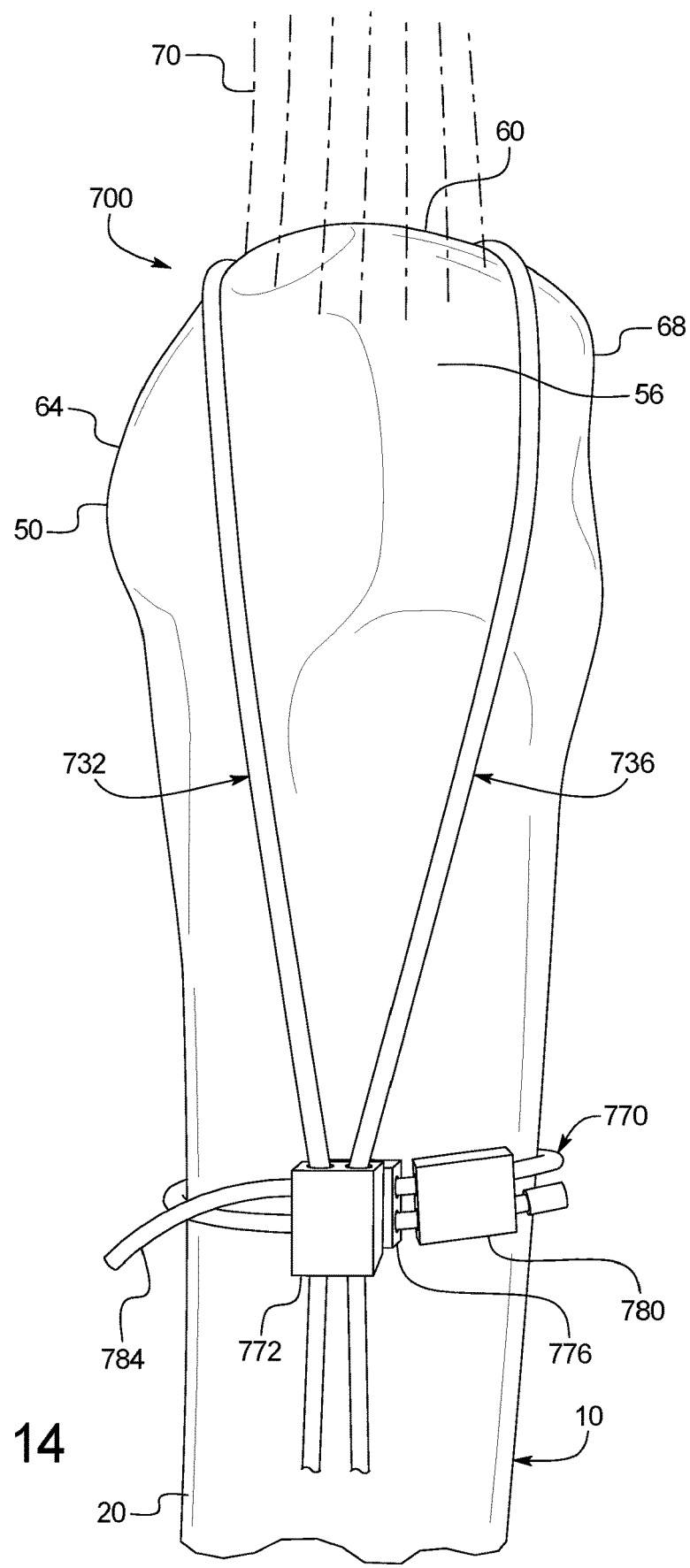
FIG. 14 is a fragmentary lateral perspective view of the upper portion of the femur (including the trochanter) of FIG. 13 and the trochanter securement apparatus of FIG. 13, and showing this example trochanter securement apparatus secured to the femur.

FIGS. 13 and 14 illustrate another example embodiment of a direct anterior hip replacement trochanter securement apparatus of the present disclosure. This example direct anterior hip replacement trochanter securement apparatus is generally indicated by numeral 700, and is referred to herein for brevity as the trochanter securement apparatus 700 or the apparatus 700. This example trochanter securement apparatus 700 generally includes: (1) an implant connector 710; (2) a trochanter engager 730; and (3) a trochanter engager securer 770.

More specifically, in this example embodiment, the implant connector 710 includes a fastener 712 removably connectable to the implant 80. The implant 80 defines an opening (not shown) and has inner threads (not shown) extending into that opening. In this example, the fastener 712 includes a head 714 and a shaft (not shown) extending from the head 714. The shaft includes outer threads (not shown). The fastener 712 extends through a bracket 720. The bracket 720 is configured to hold part of the trochanter engager 730. In this example embodiment, the fastener 712 and the bracket 720 are made from a titanium alloy or a stainless steel; however, it should be appreciated that the fastener 712 and the bracket 720 can be made from other suitable materials in accordance with the present disclosure. It should also be appreciated that the fastener and the bracket 720 can be otherwise suitably configured and sized in accordance with the present disclosure. It should be appreciated that in one such alternative embodiment, the fastener includes a head that defines one or more channels through which the cable can be inserted. In various such embodiments, the head defines multiple different channels to enable selection of the appropriate channels based on the respective anatomy.

In this example embodiment, the trochanter engager 730 includes a cable 731 extending through and held by the bracket 720. The cable includes a first section 732 and a second suture 736. The second section 732 and the second section 736 are flexible members that function like the first suture 132 and the second suture 136 described above and are thus not described again for brevity. The first section 732 and the second section 736 of the cable include similar sections that preform similar functions as the sutures 132 and 136 described above.

Accordingly, the first section 732 and the second section 736 of the cable collectively function to respectively engage the various portions of the trochanter 50 to: (a) provide support for the trochanter 50; (b) provide a link between the implant 80 and various distal points of the trochanter 50 to repair muscle or bone attachments; (d) provide oppose deforming forces to the soft tissue attachments of any fractured portion of the trochanter 50; (e) restore anatomic configuration of the trochanter 50; and (f) maintain a mechanical environment to facilitate healing of the trochanter 50.

In this example embodiment, the cable is made from a stainless steel filament and may be braided; however, it should be appreciated that the cable can be made from other suitable materials in accordance with the present disclosure. It should also be appreciated that: (1) the cable can be otherwise suitably configured and sized in accordance with the present disclosure; (2) the quantity of cables may vary in accordance with the present disclosure; and (3) the quantity of sections of the cables and the specific functions of those sections of the cables may vary in accordance with the present disclosure.

In this example embodiment, the trochanter engager securer 770 includes: (1) cable receiver 772; (2) a first cable receiver 776; (3) a second cable receiver 880; and (4) a cable 884. The cable receiver 772 is configured to receive and securely grip (via crimping) and hold the cable section 732 and 736 inserted through the openings in the cable receiver 772. Otherwise, the trochanter engager securer 770 is similar to the trochanter engager securer 170 and not further described again for brevity.

It should be appreciated that the positions of the suture receiver 772 and the first cable receiver 776 can be switched (such as shown in FIGS. 22, 23, 24, and 25) to bring the sutures closer to the posterior side of the femur (including the trochanter). It should also be appreciated that one end of the cable 784 can have a bead (such as shown in FIG. 21) for engagement with the second cable receiver 780. It should also be appreciated that the second cable receiver 780 can be alternatively positioned such as on the opposite side of the femur (such as shown in FIGS. 22, 23, 24, and 25). It should further be appreciated that the trochanter engager securer 770 can be positioned closer to the trochanter (such as shown in FIGS. 22, 23, 24, and 25) to bring the sutures closer to the posterior side of the femur (including the trochanter).

In this example embodiment, the trochanter engager securer 770 is made from a stainless steel; however, it should be appreciated that the trochanter engager securer 770 can be made from other suitable materials in accordance with the present disclosure. It should also be appreciated that the trochanter engager securer 770 can be otherwise suitably configured and sized in accordance with the present disclosure.

FIGS. 13 and 14 show the trochanter securement apparatus 700 after this apparatus 700 has be secured to the femur 10 and to the implant 80 that is inserted in the femur 10. More specifically, FIGS. 13 and 14 show the apparatus 700 after the implant connector 710 has been securely connected to the implant 80, after the trochanter engager 730 including the trochanter gripper 740 has been positioned to engage the trochanter 30 of the femur 10, after the trochanter engager securer 770 has been attached to an intermediate portion 20 of the femur 10 below the trochanter 50, and after the trochanter engager 730 has been securely connected to the trochanter engager securer 770. This example embodiment may be employed for smaller or more significant fractures or to prevent fractures, where the cables 763 and 736 function together on the trochanter. This example embodiment is also easy to install and use, and can be used regardless of final stem seating position. This example embodiment is also relatively simple and inexpensive to manufacture.

Figure 22:
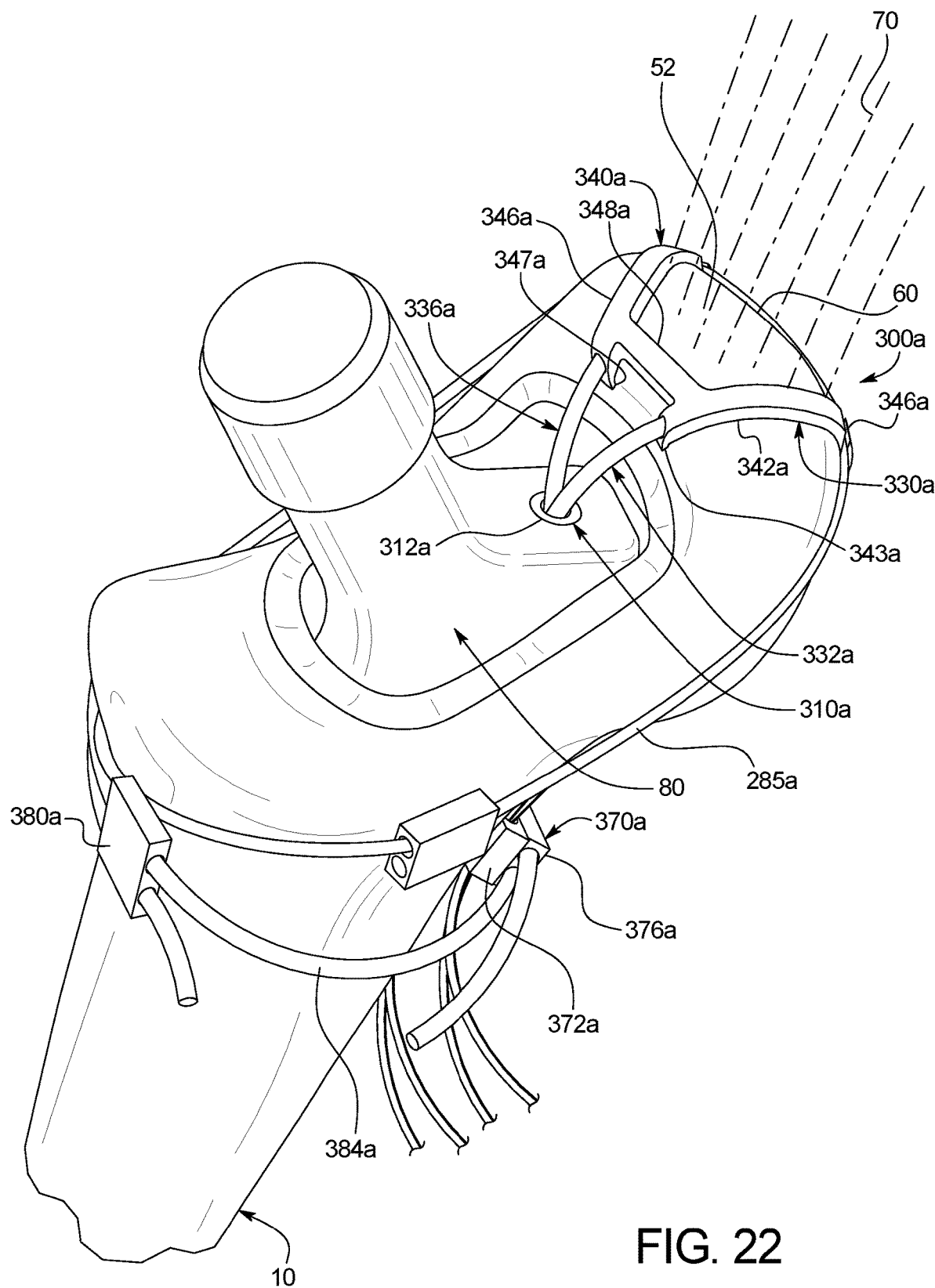
FIG. 22 is a fragmentary anterolateral perspective view of an upper portion of a femur (including the trochanter), a portion of part of an implant shown inserted into the femur, and a trochanter securement apparatus of another example embodiment of the present disclosure, and showing this example trochanter securement apparatus secured to the implant and secured to the femur.
Figure 23:
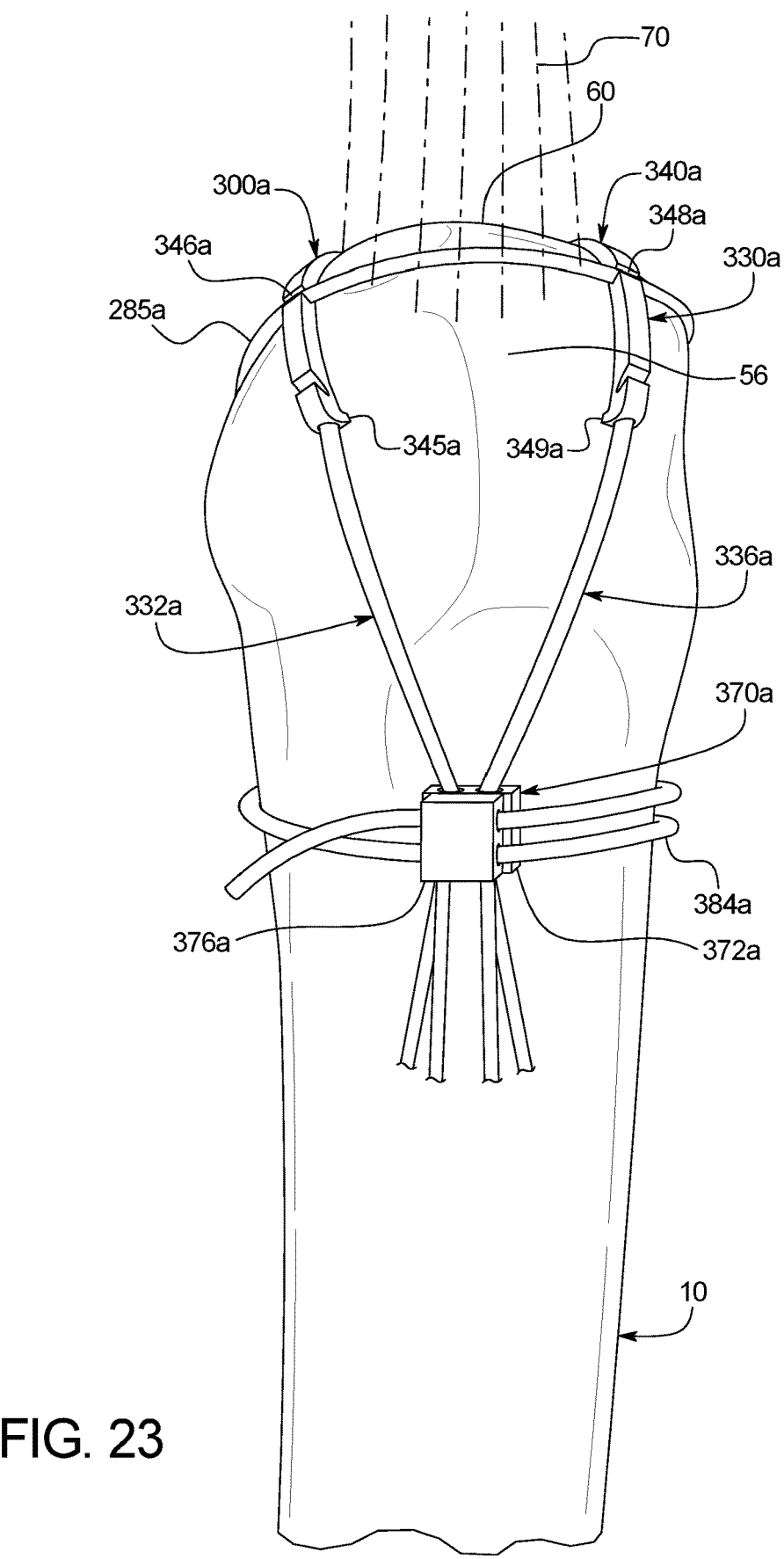
FIG. 23 is a fragmentary lateral perspective view of the upper portion of the femur (including the trochanter) of FIG. 22 and the trochanter securement apparatus of FIG. 22, and showing this example trochanter securement apparatus secured to the femur.

FIGS. 22 and 23 illustrate another example embodiment of a direct anterior hip replacement trochanter securement apparatus of the present disclosure. This example is similar to the example direct anterior hip replacement trochanter securement apparatus of FIGS. 5 and 6. This example direct anterior hip replacement trochanter securement apparatus is generally indicated by numeral 300A, and is referred to herein for brevity as the trochanter securement apparatus 300A or the apparatus 300A. This example trochanter securement apparatus 300A generally includes: (1) an implant connector 310A; (2) a trochanter engager 330A; and (3) a trochanter engager securer 370A.

More specifically, in this example embodiment, the implant connector 310A includes a fastener 312A removably connectable to the implant 80. The fastener 312A in this example embodiment is identical to the fastener 110 explained above and is thus not described again for brevity. In this example embodiment, the fastener 312A is made from a titanium alloy; however, it should be appreciated that the fastener 312A can be made from other suitable materials in accordance with the present disclosure. It should also be appreciated that the fastener can be otherwise suitably configured and sized in accordance with the present disclosure.

In this example embodiment, the trochanter engager 330A includes a first suture 332A, a second suture 336A, and a trochanter gripper 340A. The first suture 332A and the second suture 336A are configured to extend through the trochanter gripper 340A and to hold the trochanter engager 330A in place.

The first suture 332A and the second suture 336A are both elongated flat flexible members in this example embodiment. The first suture 332A includes: (a) a first section (not labeled): (b) a second section (not shown); (c) a third section (not shown); (d) a fourth section (not shown); (e) a fifth section (not labeled); and (f) a sixth section (not labeled). Likewise, the second suture 336 includes: (a) a first section (not labeled); (b) a second section (not shown); (c) a third section (not shown); (d) a fourth section (not shown); (e) a fifth section (not labeled); and (f) a sixth section (not labeled).

In this example embodiment, the trochanter gripper 340A is configured to engage each of the medial interior portion 52, the superior portion 60, and the lateral portion 56 of the trochanter 50. The trochanter gripper 340A includes a first tube 342A, a second tube 346A, and a connector 348A that suitably connects the first tube 342A and the second tube 346A. The first tube 342A and the second tube 346A each define internal suture passageways (not shown or labeled) through which the respective sutures 332A and 336A can be threaded through. The trochanter gripper 340A and specifically the first tube 342A, the second tube 346A, and the connector 348A provide increased engagement surface areas for engagement with the medial interior portion 52, the superior portion 60, and the lateral portion 56 of the trochanter 50. It should also be noted that the connecter 348A is positioned such that it does not interfere with the muscle 70. In other words, the tubes 342A and 346A and the connector 348 define a space for the muscles 70 and specifically the abductor muscles.

Additionally, the trochanter gripper 340A includes a plurality of teeth configured to engage the trochanter 50. Specifically, the first tube 342A includes teeth 343A and 345A and the second tube 346A includes teeth 347A and 349A. The teeth 343A and 347A are configured to engage the medial interior portion 52 of the trochanter 50. The teeth 345A and 349A are configured to engage the lateral portion 56 of the trochanter 50. These teeth 343A, 345A, 347A, and 349A provide further increased engagement with the anterior portion 52 and the posterior portion 56 of the trochanter 50.

In this embodiment, the trochanter gripper 340A defines a plurality of aligned transverse slots or notches configured to receive an transversely extending additional attachment cable 385A. Specifically, in this example embodiment, the first tube 342A includes transversely extending slot 346A and the second tube 346A includes transversely extending slot 348A. The slots 346A and 348A are configured to receive (with the walls that define the slots engaging) the transversely extending cable 385A for additional securement of and increased engagement with the posterior portion 56 of the trochanter 50. The cable 285A can be secured as shown or otherwise suitably secured. Although not labeled, the trochanter gripper 340A defines a second set of aligned transverse slots or notches configured to additionally or alternatively receive another transversely extending additional attachment cable. The quantity of sets of slots may thus vary in accordance with the present disclosure.

It should be appreciated that such transversely extending slots and cable can be employed in various other embodiments of the trochanter gripper and the trochanter engager of the present disclosure. It should be appreciated that the slots or notches are shown in a lateral aspect. These slots or notches can be additionally or alternatively present in both the anterior and posterior sections of the gripper. The slots or notches each have a suitable depth to facilitate, if desired, the use of the additional cable or suture placed in a circumferential fashion such as shown. The slots or notches can be oriented in such a manner such that their respective openings face proximally and thereby prevents distal migration of the cable or suture once it is engaged.

In this embodiment, the first section of the first suture 332A and the first section of the second suture 336A are respective end sections and are securely attached to the implant connector as described above.

The second section of the first suture 332A and the second section of the second suture 336A are respective intermediate sections and are configured to extend through respective anterior portions of the first tube 342A and the second tube 346A of the trochanter gripper 340A.

The third section of the first suture 332A and the third section of the second suture 336A are respective intermediate sections and are configured extend through respective top portions the first tube 342A and the second tube 346A of the trochanter gripper 340A.

The fourth section of the first suture 332A and the fourth section of the second suture 336A are respective intermediate sections and are configured to extend through respective posterior portions of the trochanter gripper 340A.

The fifth section of the first suture 332A and the fifth section of the second suture 336A are respective intermediate sections and are configured to extend downwardly toward the trochanter engager securer 370A, but at much closer respective positions to the posterior side of the trochanter.

The sixth section of the first suture 332A and the sixth section of the second suture 336A are respective end sections and are securely attached to the trochanter engager securer 370A. In this example embodiment, the sixth section of the first suture 332A and the sixth section of the second suture 336A extend through the openings in the trochanter engager securer 370 that are more adjacent to the posterior side of the trochanter and are securely attached thereto. The trochanter engager secure 370A is also much closer to the superior portion 60 of the trochanter 50 which also brings the first suture 332A and the second suture 336A much closer to the lateral side of the trochanter for better engagement. The first suture 332A and the second suture 336A thus better function to limit movement of the trochanter gripper 370A with respect to the trochanter 50. This trochanter gripper 340A further enhances the functionality of the trochanter gripper 340 described above and of the entire direct anterior hip replacement trochanter securement apparatus 340A.

In this example embodiment, the trochanter gripper 340A is made from titanium alloys; however, it should be appreciated that the trochanter gripper 340A can be made from other suitable materials in accordance with the present disclosure. It should also be appreciated that: (1) the trochanter gripper 340A can be otherwise suitably configured and sized in accordance with the present disclosure; (2) the quantity of tubes of the trochanter gripper 340A can be vary in accordance with the present disclosure; (3) the quantity of sutures configured to engage the trochanter gripper 340A can vary in accordance with the present disclosure; (4) the engagement of the sutures with the trochanter gripper 340A can vary in accordance with the present disclosure; (5) the quantity of teeth can vary in accordance with the present disclosure; and (6) the quantity and positions of the transverse slots can vary in accordance with the present disclosure.

In this example embodiment, the trochanter engager securer 370A includes: (1) suture receiver 372A; (2) a first cable receiver 376A; (3) a second cable receiver 380A; and (4) a cable 384A. As mentioned above, the trochanter engager securer 370A in this example embodiment secures the sutures 332A and 336A closer to the posterior side 56 of the trochanter. In this example embodiment, the second cable receive 380A is on the opposite side of the trochanter. In this example embodiment, the trochanter engager securer 370A is higher up on the trochanter. Otherwise, the trochanter engager secure 370A functions similar to the trochanter engager securer 170 explained above and is thus not described again for brevity.

In this example embodiment, the trochanter engager securer 370A is made from stainless steel multifilament cable; however, it should be appreciated that the trochanter engager securer 370A can be made from other suitable materials in accordance with the present disclosure. It should also be appreciated that the trochanter engager securer 370A can be otherwise suitably configured and sized in accordance with the present disclosure.

FIGS. 22 and 23 show the trochanter securement apparatus 300A after this apparatus 300A has be secured to the femur 10 and to the implant 80 that is inserted in the femur 10. More specifically, FIGS. 22 and 23 show the apparatus 300 after the implant connector 310A has been securely connected to the implant 80, after the trochanter engager 330A including the trochanter gripper 340A has been positioned to engage the trochanter 30 of the femur 10, after the trochanter engager securer 370A has been attached to a more upper portion of the femur 10 slightly below the trochanter 50, and after the trochanter engager 330A has been securely connected to the trochanter engager securer 370A. This example embodiment can be employed for smaller or more significant fractures or to prevent fractures, where the sutures 332A and 336A (or alternatively cables) and the trochanter gripper 340 function together on the trochanter. This example embodiment is also easy to install and use, and can be seated in various different positions. This example embodiment is also relatively simple and inexpensive to manufacture. It should also be appreciated that the trochanter engager securer can function as a distal anchoring point through which tension is maintained upon the more proximal trochanter engager and sutures/cable.

Figure 24:
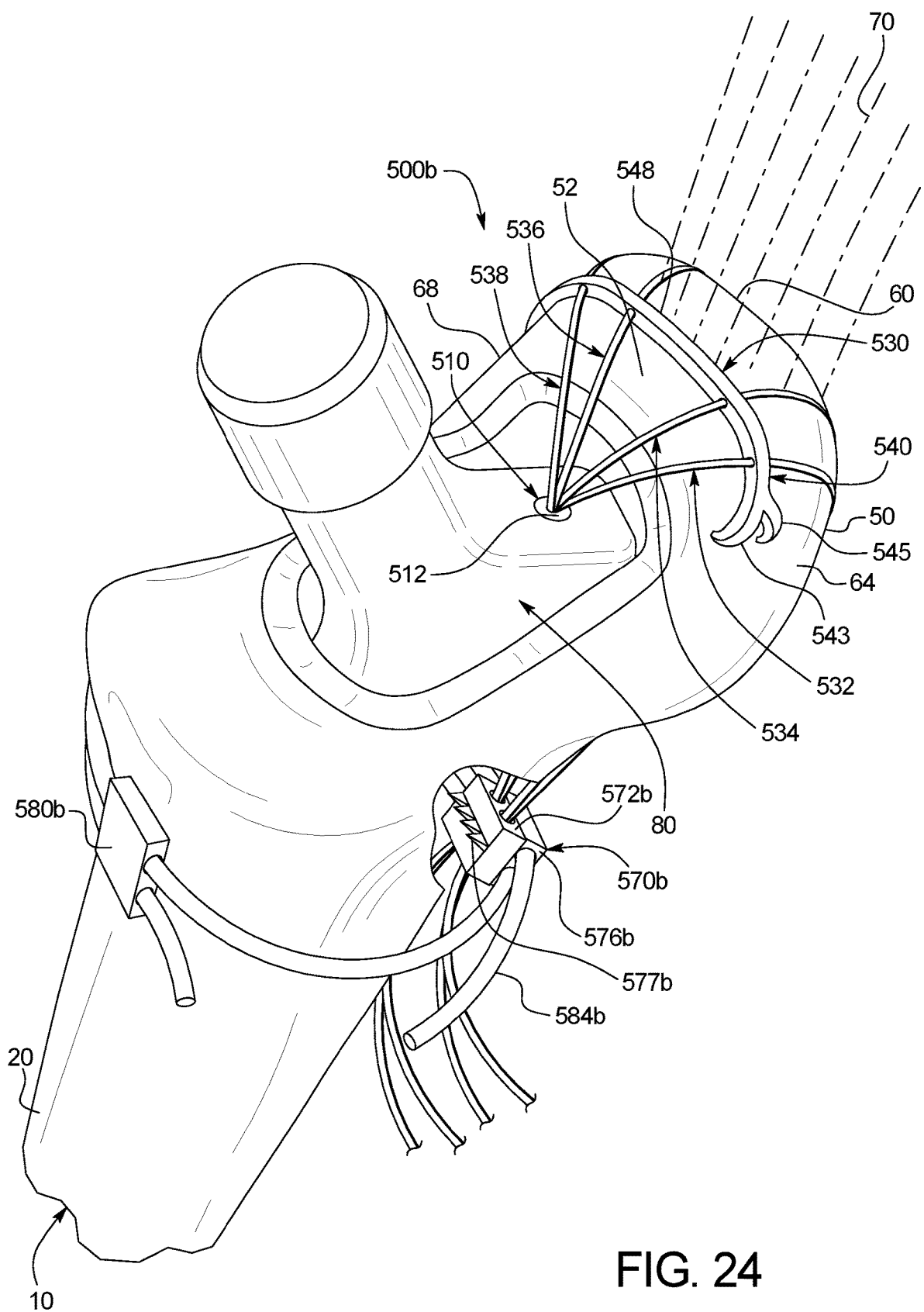
FIG. 24 is a fragmentary anterolateral perspective view of an upper portion of a femur (including the trochanter), a portion of part of an implant shown inserted into the femur, and a trochanter securement apparatus of another example embodiment of the present disclosure, and showing this example trochanter securement apparatus secured to the implant and secured to the femur. This figure has a portion of the femur broken away so that the interior teeth of the trochanter securement apparatus can be seen.
Figure 25:
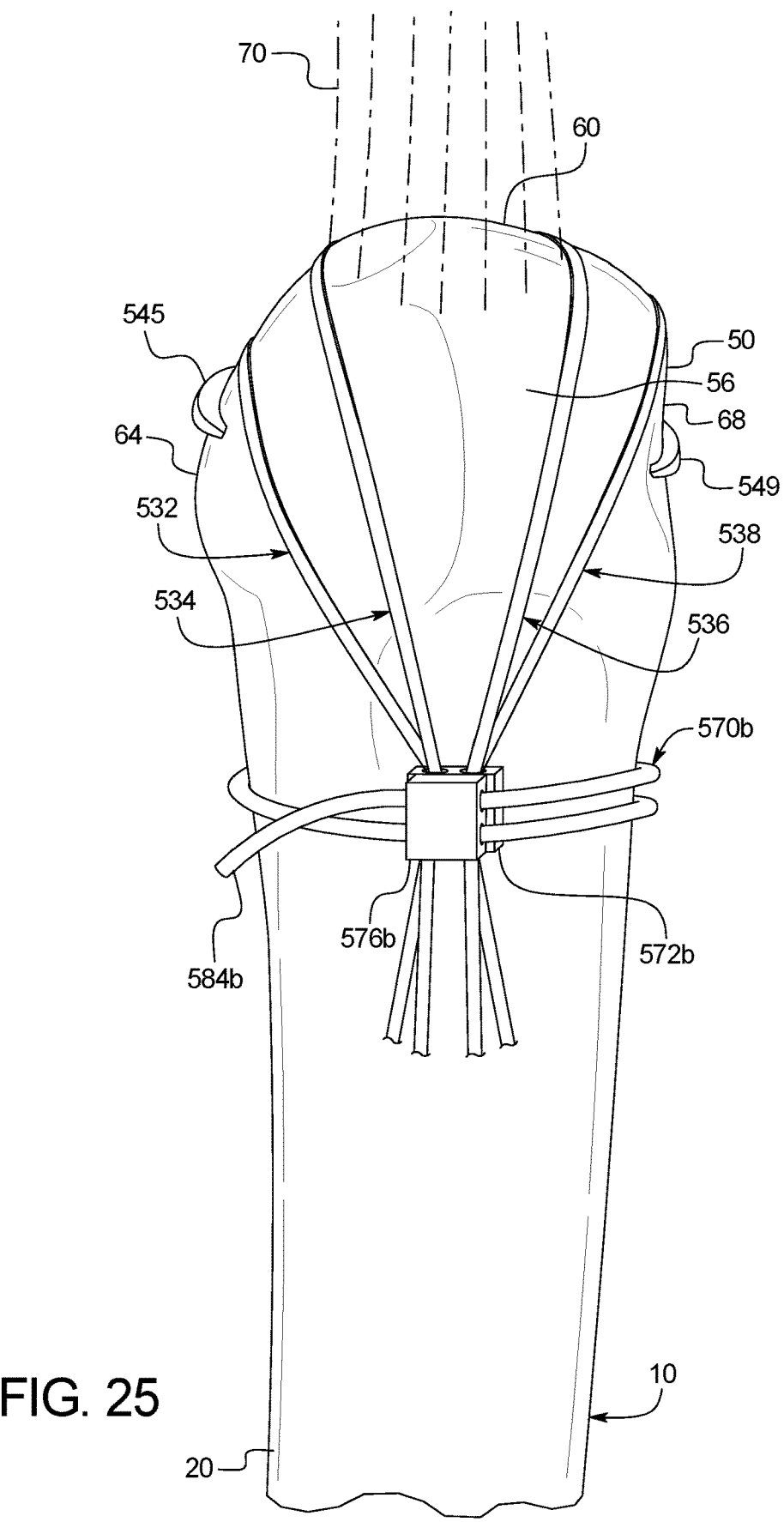
FIG. 25 is a fragmentary lateral perspective view of the upper portion of the femur (including the trochanter) of FIG. 26 and the trochanter securement apparatus of FIG. 22, and showing this example trochanter securement apparatus secured to the femur.

FIGS. 24 and 25 illustrate another example embodiment of a direct anterior hip replacement trochanter securement apparatus of the present disclosure. This example direct anterior hip replacement trochanter securement apparatus 500B is similar to the trochanter securement apparatus 500 except for the trochanter engager securer 570B. Thus, the same numbering is used for the direct anterior hip replacement trochanter securement apparatus 500B as for the trochanter securement apparatus 500. Additionally, those same components are not described again for brevity. Rather, the following description focuses on the trochanter engager securer 570B.

In this example embodiment, the trochanter engager securer 570B includes: (1) suture receiver 572B; (2) a first cable receiver 576B; (3) a second cable receiver 580B; and (4) a cable 584B. The trochanter engager securer 570B and specifically the suture 572B secures the sutures 532, 534, 536, and 538 closer to the posterior side 56 of the trochanter 50. The trochanter engager securer 570B also includes a plurality of teeth 577B configured to engage the posterior side 56 of the trochanter 50. In this example embodiment, the second cable receive 580A is on the opposite side of the trochanter. In this example embodiment, the trochanter engager securer 570B is also higher up on the trochanter.

In this example embodiment, the trochanter engager securer 570B is made from titanium alloys; however, it should be appreciated that the trochanter engager securer 570B can be made from other suitable materials in accordance with the present disclosure. It should also be appreciated that the trochanter engager securer 570B can be otherwise suitably configured and sized in accordance with the present disclosure.

FIGS. 24 and 25 show the trochanter securement apparatus 500B after this apparatus 500B has be secured to the femur 10 and to the implant 80 that is inserted in the femur 10. More specifically, FIGS. 24 and 25 show the apparatus 500B after the implant connector 510 has been securely connected to the implant 80, after the trochanter engager 530 has been positioned to engage the trochanter 30 of the femur 10, after the trochanter engager securer 570B has been attached to the femur 10 slightly below the trochanter 50, and after the trochanter engager 530 has been securely connected to the trochanter engager securer 570B. This example embodiment may be employed for smaller or more significant fractures or to prevent fractures, where the sutures 532, 534, 536, and 538 (or alternatively cables) and the trochanter gripper 540 function together on the trochanter. This example embodiment is also easy to install and use, and can be seated in various different positions. This example embodiment is also relatively simple and inexpensive to manufacture. It should also be appreciated that this example embodiment is configured to prevent anterior or posterior trochanteric migration with the additional anterior and posterior teeth. Similarly, it can also engage smaller anterior or posterior fragments. Thus, this example embodiment may be particularly suited for addressing multiple types of fractures.

Figure 15:
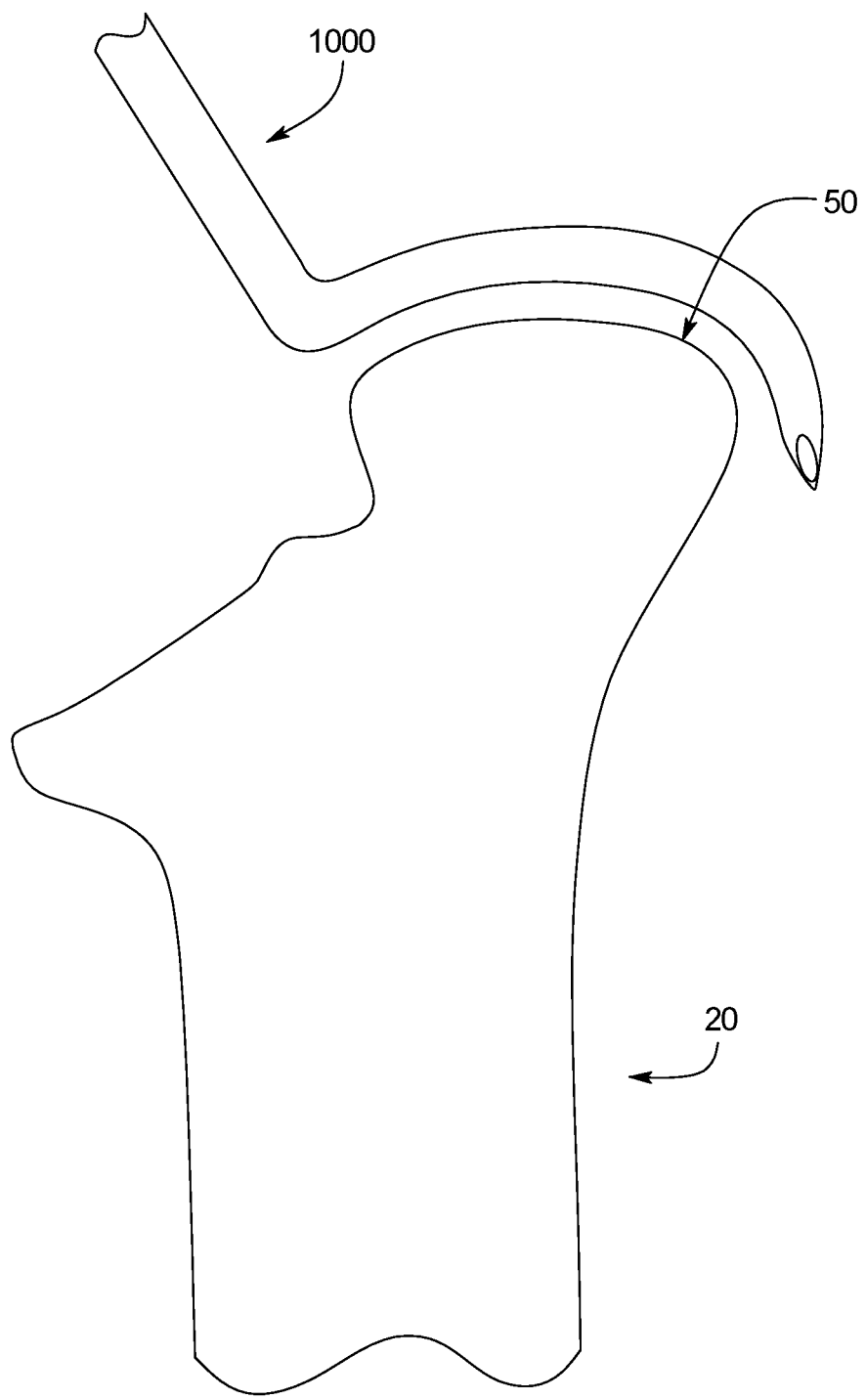
FIG. 15 is a side view showing an example tool of the present disclosure usable to attach a trochanter securement apparatus to a trochanter.

FIG. 15 illustrates an example embodiment of first installation tool 1000 that can be used for placement of a trochanter securement apparatus of the present disclosure. This example tool 1000 includes a handle (not labeled) and one or more prongs (not labeled). The prongs: (1) can be any suitable shape; (2) can be used to create openings in the tissue (such as the abductor tendons or muscles) for inserting the cables or sutures through the tissue; (3) can be pointed or have sharp edges; (4) can have openings or grooves for receiving or guiding the cables or sutures; and/or (5) can be of any suitable length and curvature. One goal of this example tool is to facilitate expedient passage of sutures and or cables for lateral retrieval on the lateral aspect of the hip. This tool can also facilitate appropriate spacing of sutures or cables to achieve solid purchase or engagement. If a securement device including a more plate-like structure, is used it can also facilitate appropriate plate position.

Figure 16:
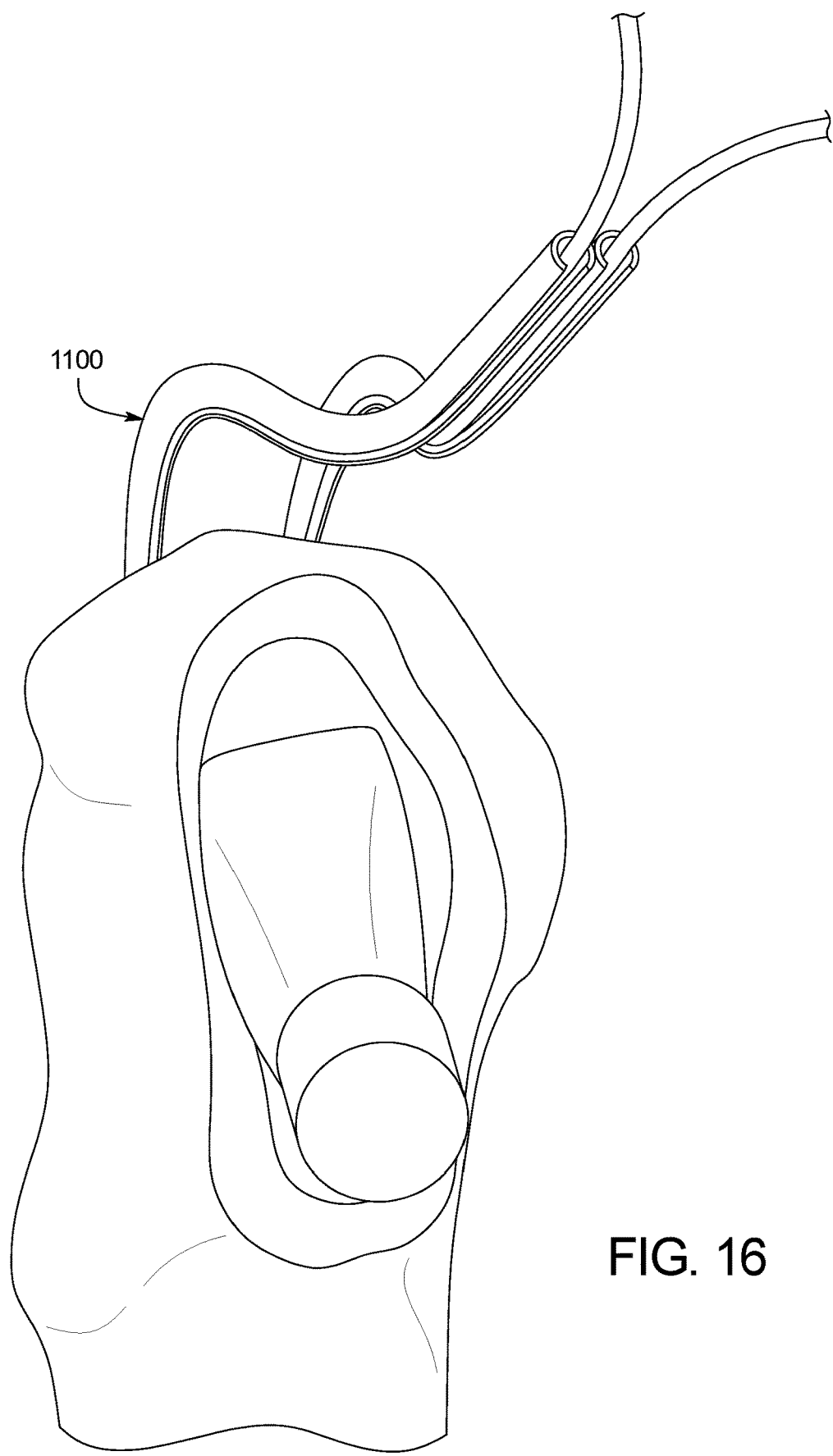
FIG. 16 is a fragmentary top view showing another example tool of the present disclosure usable to attach a trochanter securement apparatus to a trochanter.

FIG. 16 illustrates an example embodiment of a second installation tool 1200 that can be used for placement of a trochanter securement apparatus of the present disclosure. This example installation tool 1100 includes a handle (not shown for clarity) and two prongs (not labeled). The prongs have curved contours to facilitate passage over the tip of the greater trochanter. The prongs are somewhat semi-circular cannulas and are opened at the respective bottom portions such the sutures or cables (not labeled) can be passed through such cannulas and such that the prongs and the entire installation tool 1100 can be removed without disruption of the cables or sutures. One goal of this tool is to facilitate expedient passage of sutures and or cables for lateral retrieval on the lateral aspect of the hip. This device can also facilitate appropriate spacing of sutures or cables to achieve solid purchase or engagement. If a securement device including a more plate-like structure, is used it can also facilitate appropriate plate position.

Figure 17:
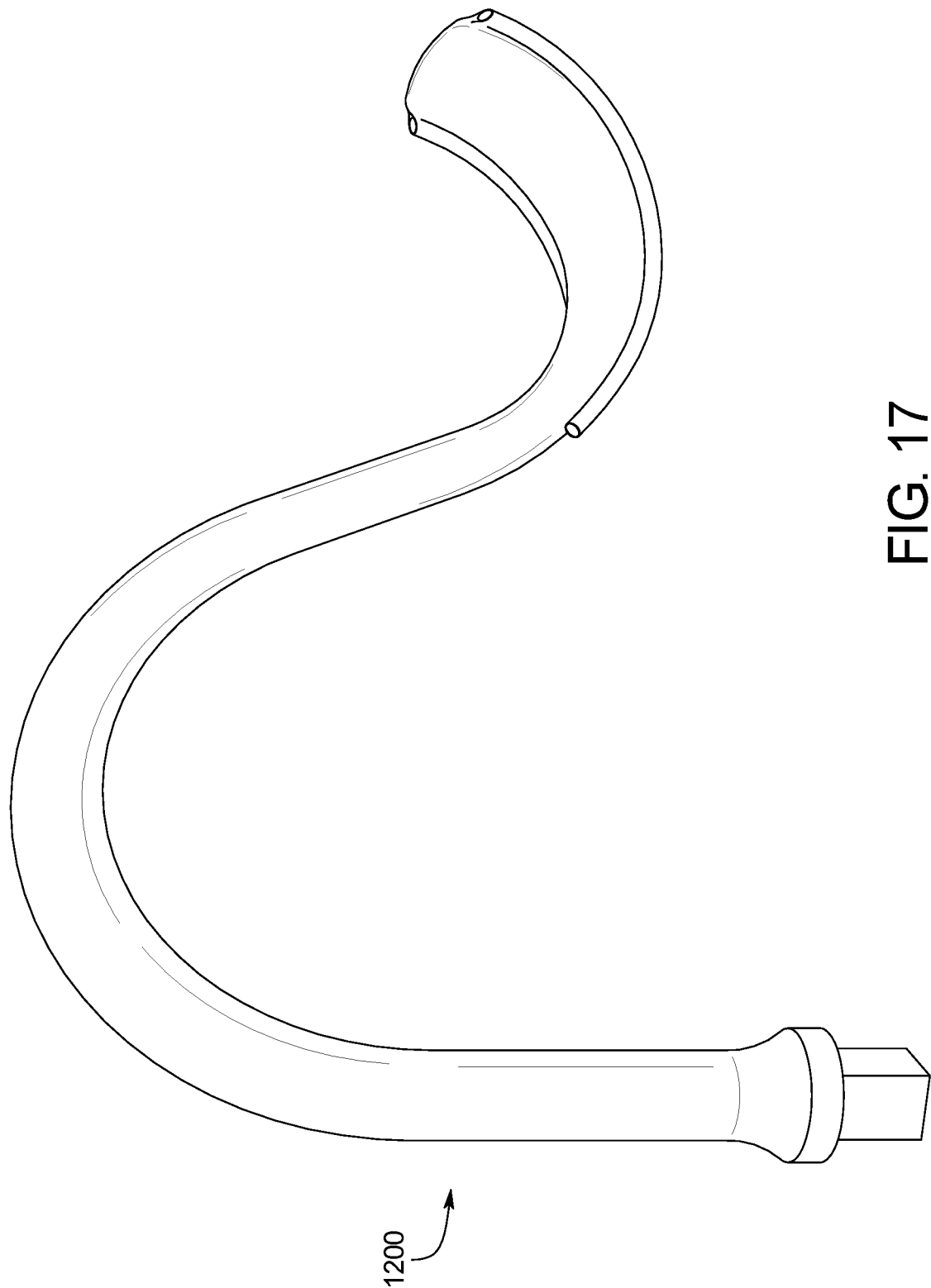
FIG. 17 is a side view showing another example tool of the present disclosure usable to attach a trochanter securement apparatus to a trochanter.
Figure 18:
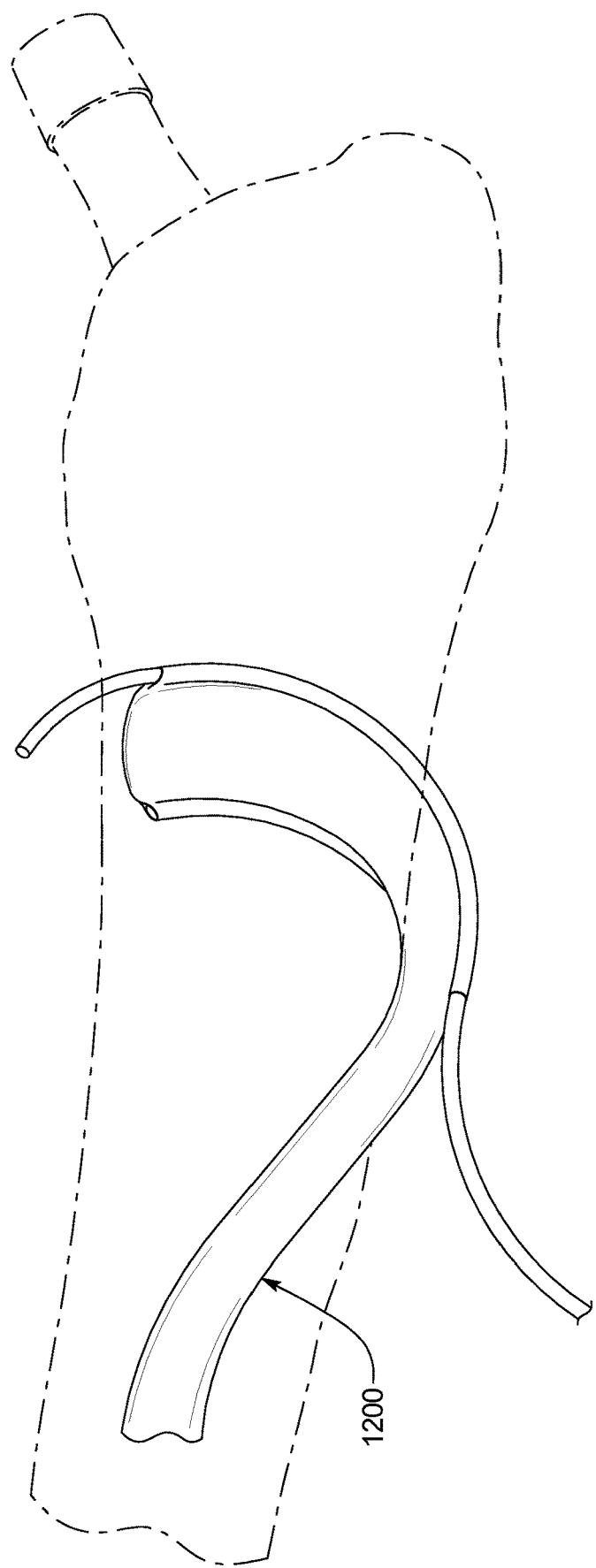
FIG. 18 is a lateral view showing a fragmentary view of the example tool of FIG. 17 being used to attach a trochanter securement apparatus to a trochanter.

FIGS. 17 and 18 illustrate an example embodiment of a third installation tool 1200 that can be used for placement of a trochanter securement apparatus of the present disclosure. This example installation tool 1200 includes a square mounting member (not labeled) on one end. The mounting member is configured to be attached to an operative table (not shown). The opposite end includes a curved, flattened, lifting hook (not labeled) bordered by two tubular cannulas (not labeled). These cannulas follow a same contour/shape as the hook, and are configured to facilitate the passage of circumferential cable(s) around the femur, distal to the lesser trochanter. These cables ultimately assist in the securement of the trochanter engaging apparatus such as described above. By using this hook type tool, which maintains the femur in a position of external rotation and extension during femoral preparation, circumferential distal anchoring cable(s) can be placed without repositioning the femur. By avoiding the need to reposition the femur for cable passage, this tool can reduce surgical time and improve patient safety. While this hook type tool can be placed outside the vastus lateralis, this hook type tool can be placed between the vastus literalist and the bone to facilitate close positioning of cables or sutures near the bone. Furthermore, the radius of curvature or the length of the cannulated portion can be further modified to facilitate cable retrieval during circumferential passage.

Figure 19:
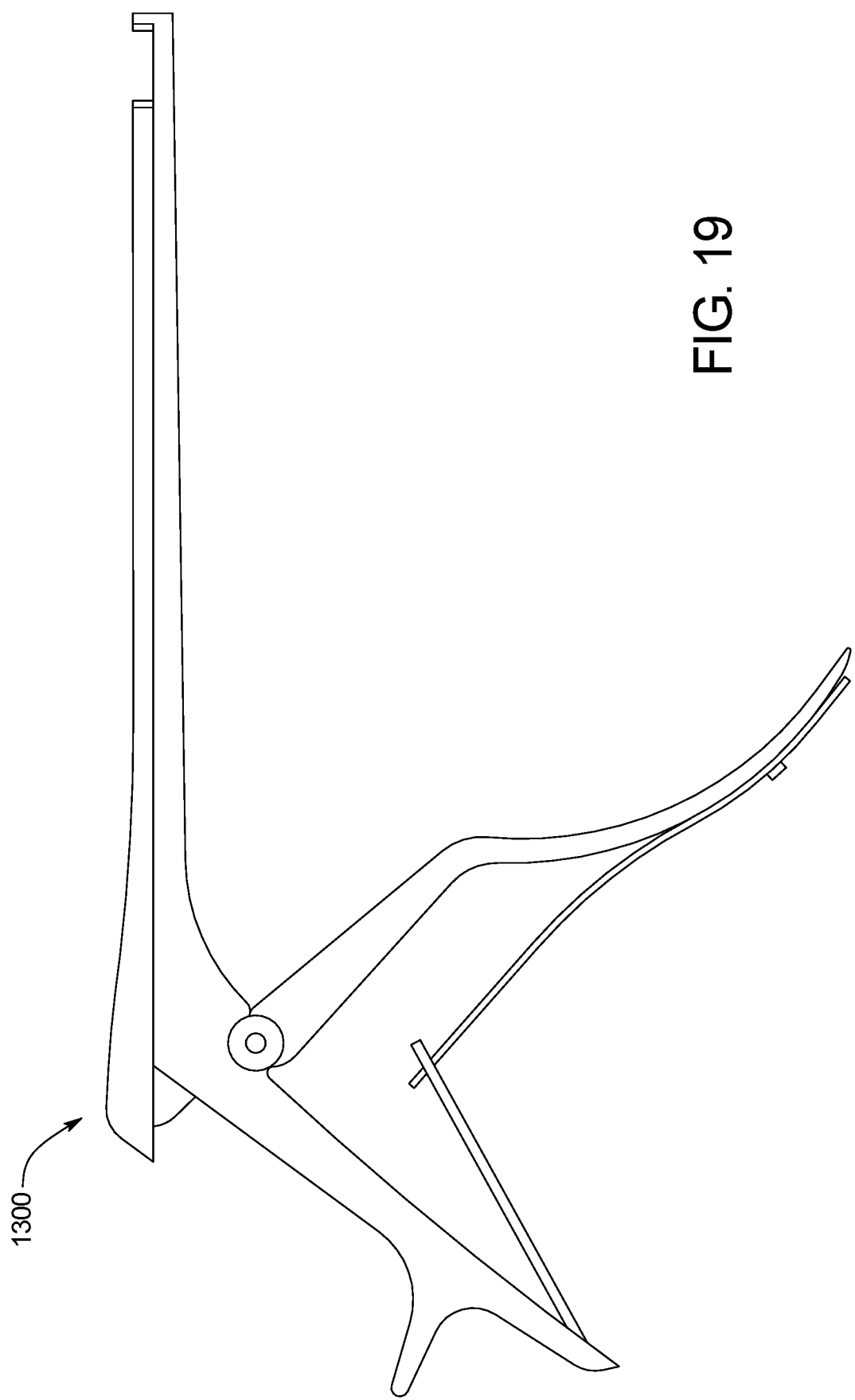
FIG. 19 is a side view showing another example tool of the present disclosure usable to attach a trochanter securement apparatus to a trochanter.
Figure 20:
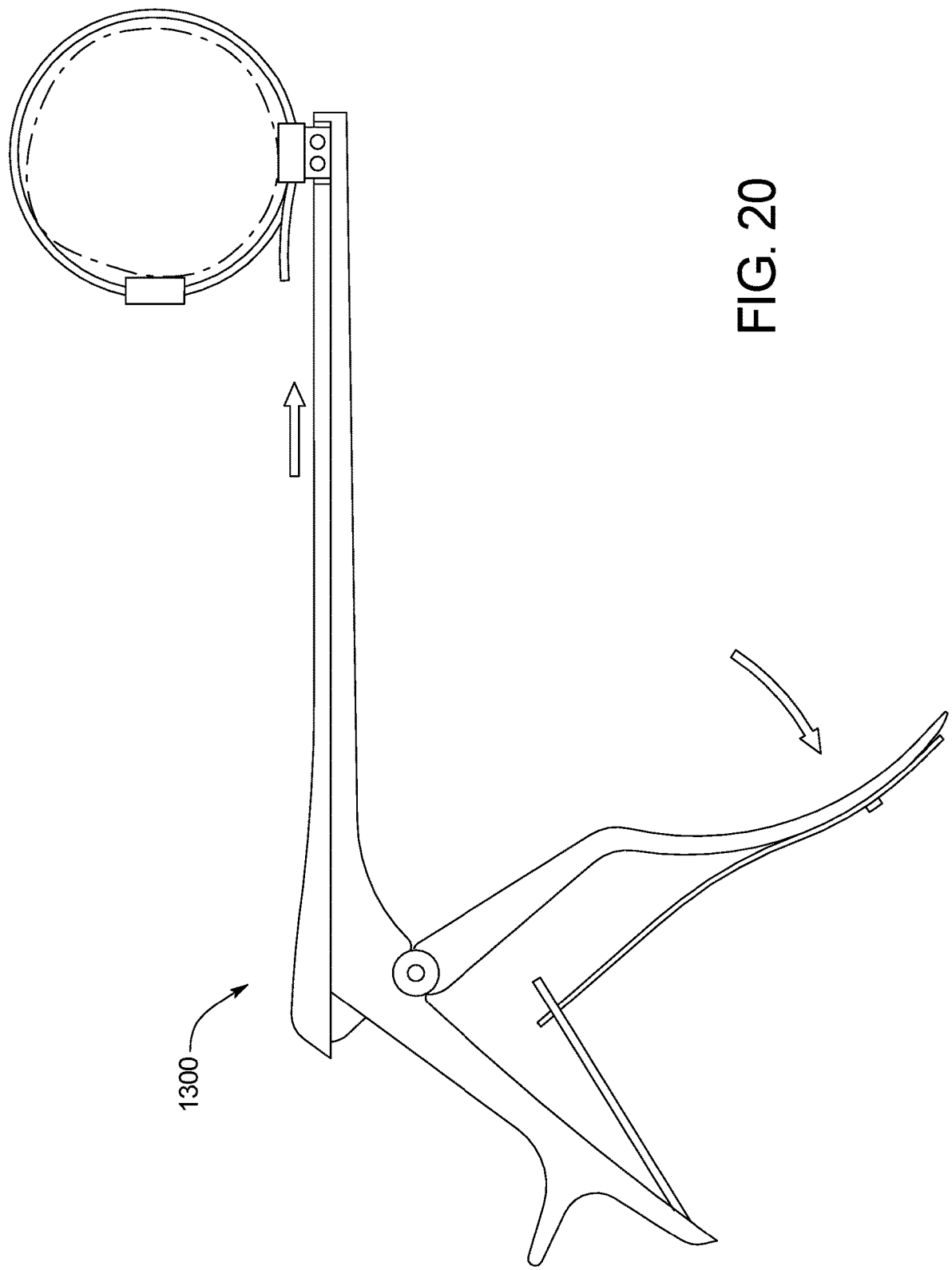
FIG. 20 is a cross-sectional view of a femur showing the example tool of FIG. 18 being used to attach a trochanter securement apparatus to a trochanter of the femur.

FIGS. 19 and 20 illustrate an example embodiment of a fourth installation tool 1300 that can be used for placement of a trochanter securement apparatus of the present disclosure. This example installation tool 1300 includes a handle (not labeled), a spring mechanism (not labeled), and an cable sleeve compressor (not labeled) having a tip end (not labeled). These components cooperate to be positioned to and to selectively apply compressive forces at the tip of the tool and the ability to compress a cable sleeve for cables or sutures coursing through a cable sleeve superiorly to inferiorly on the lateral aspect of the hip. This installation tool is configured to crimp a lateral cable sleeve from an anterior approach incision, thereby eliminating the need for an accessory lateral incision in various instances.

FIG. 21 illustrates an example technique that can be used for placement of a trochanter securement apparatus of the present disclosure. This example utilizes a Hewson-type suture passer 1400 (or similar device) to facilitate retrieval of sutures passed over the top of the greater trochanter. The loop-engaged sutures can be pulled through the lateral-based sleeve prior to tensioning and fracture compression. It should be appreciated as described above that the suture receiver can be positioned closer to the femur to bring the sutures closer to the lateral side of the femur.

Figure 26:
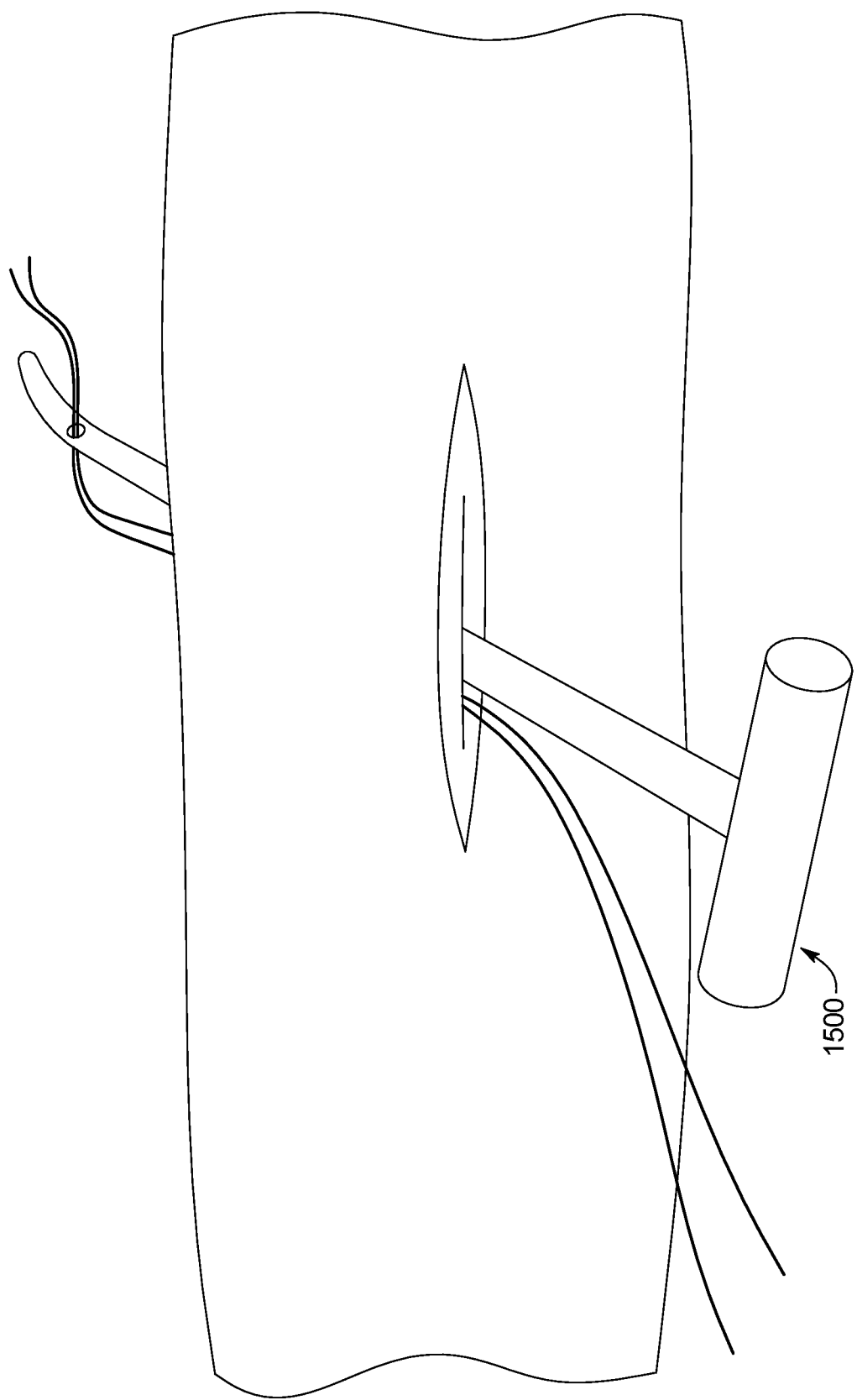
FIG. 26 is a side view showing another example tool of the present disclosure usable to attach a trochanter securement apparatus to a trochanter.

FIG. 26 illustrates an example embodiment of a fifth installation tool 1500 that can be used for placement of a trochanter securement apparatus of the present disclosure. This example installation tool 1500 includes a handle (not labeled) an needle (not labeled) having a first end connected to the handled and a second free end (not labeled) configured to receive one or more sutures. This installation tool is configured to receive a suture from the trochanteric securement apparatus and direct that suture or cable through the lateral skin. Subsequently, the surgical technique can include utilizing these sutures exiting the skin laterally to attach to or thread through a tensioner, which can then be passed over this suture or cable back through the skin down to the sleeve for tensioning and crimping of the trochanteric engaging portion.

It should be appreciated from the above that the trochanter securement apparatus of various embodiments of the present disclosure may alternatively or additionally be employed for certain muscle repairs for such muscles attaching in the anatomic vicinity of the piriformis fossa or near the ultimate seating position of the stem shoulder.

It should be appreciated from the above that the trochanter securement apparatus of various embodiments of the present disclosure may include a prosthetic joint or internal stabilization device that engages and becomes unified with the bone through a biologic and/or mechanical mechanism.

It should be appreciated from the above that the trochanter securement apparatus of various embodiments of the present disclosure may include any suitable strong flexible members such as sutures or cables (attached to such anchoring devices) that are positionable in close approximation to adjacent tissue for purposes of surgical stabilization.

It should be appreciated that the trochanter securement apparatus of various embodiments of the present disclosure may include any suitable strong flexible members such as sutures or cables that are routed through surgically constructed bone tunnels or tubes.

It should be appreciated the trochanter securement apparatus may of various embodiments of the present disclosure include any suitable strong flexible members such as sutures or cables that are tensioned upon itself with a tied knot or additionally a suitable crimping sleeve.

It should be appreciated from the above that the trochanter securement apparatus of various embodiments of the present disclosure may include any suitable strong flexible members such as sutures and or cables that are terminally tensioned and anchored by engaging them with screws or anchors in adjacent bone.

It should be appreciated from the above that the joint replacement apparatus pf the present disclosure may be employed for total elbow joint replacement system, a shoulder joint replacement system, a knee joint replacement system, or an intramedullary rod.

It should be appreciated from the above that the trochanter securement apparatus of various embodiments of the present disclosure may include a suture or cable anchoring device that engages with or into a joint replacement prosthesis, intramedullary rod, or compression screw. In certain such embodiments, the fastener may have as a part of its composition or may separately interface with a sleeve to allow for cable routing or compression. In certain such embodiments, this sleeve by its coupling with the fastener may be secured in varied positions around the axis of the fastener to position cables and or sutures into an substantial quantity of different positions and orientations It should be appreciated from the above that the trochanter securement apparatus of various embodiments of the present disclosure may include any suitable strong flexible members such as cables or sutures originating in the anchor in various quantities and combinations.

It should be appreciated from the above that the trochanter securement apparatus of various embodiments of the present disclosure, owing to the unique anatomic exposures of anterior approach hip replacement, may include any suitable strong flexible members such as cables or sutures that closely traverse from their anchor origin first along the inner aspect of the greater trochanter, followed by the superior aspect of the greater trochanter, followed by the lateral aspect of the greater trochanter, followed by the more distal aspect of the femur. In various such embodiment, multiple additional cables or sutures may be passed along other surfaces of the greater trochanter of the femur, including its anterior and posterior aspects.

It should be appreciated from the above that the trochanter securement apparatus of various embodiments of the present disclosure may include cables or sutures placed through larger diameter conduits. In various embodiment, such conduits may be fashioned to decrease the force per unit area upon surrounding tissue and channel wires or sutures to the appropriate anatomic location. This reduction will reduce the risk of device cutout and subsequent construct failure. In various such embodiments, owing to the unique features of anterior approach hip exposure, this conduit may facilitate appropriate position of the cables or sutures relative to the trochanteric anatomy, maintaining appropriate position of separate cables or sutures relative to one another and to the anatomic shape of the bone.

It should be appreciated from the above that the trochanter securement apparatus of various embodiments of the present disclosure may include such conduits linked to form a unit or web around the bony trochanteric anatomy, from the interior aspect of the trochanter, the anterior and posterior aspects of the trochanter, and the lateral aspect of the trochanter.

It should be appreciated from the above that the trochanter securement apparatus of various embodiments of the present disclosure may include such links (between various pieces of conduit) that are solid or modular in nature.

It should be appreciated from the above that the trochanter securement apparatus of various embodiments of the present disclosure may include two spaced apart parallel, nearly parallel, or transverse pieces of conduit linked by an orthogonal modular crosslink, facilitating the ability to adjust to space between conduit to varied widths.

It should be appreciated from the above that the trochanter securement apparatus of various embodiments of the present disclosure may include fixed or adjustable conduits that approximate the shape of a claw or web that envelops the bone of the greater trochanter, while maintaining appropriate cutouts for the unique anatomic relationships the are present in anterior approach hip replacement.

It should be appreciated from the above that the trochanter securement apparatus of various embodiments of the present disclosure may include a sutures or cables traversing the contours of the greater trochanter and the abductor muscle that are utilized to create a tension band construct. In various such embodiments, cables or sutures originating from an anchor interfacing at the threaded shoulder of the prosthesis may traverse the greater trochanter from its interior aspect, through the abductor tendons on its superior aspect, and follow closely its contours in the lateral aspect to a point more distal on the lateral femur. Such sutures or cables may be tensioned from a distal point to apply a compressive force upon the trochanter.

It should be appreciated from the above that the trochanter securement apparatus of various embodiments of the present disclosure may include a cable apparatus may be passed around a femur circumferentially. Such cable apparatus may be equipped with multiple sleeves. In various such embodiments, the first sleeve may be threaded with each end of the cable to allow the cable to form a loop. In this embodiment, once a loop is formed and tensioned, this sleeve may be crimped and deformed to maintain tension upon the loop in close proximity to the femur. A second sleeve on this cable may also contains a crimp, allowing it's position to be secured in fixed fashion at given point on the circumference of the cable loop. This second sleeve may be fixed in attachment to a third sleeve, oriented perpendicularly to the first two sleeves. The conduits in this third sleeve may be utilized to accept suture or cable from another location. In one such example, cables or sutures passed proximally from a cable or suture anchor linked to the shoulder of a femoral prosthesis may be passed from the inner aspect of the greater trochanter through the abductor tendons via a claw-shaped conduit, then be tensioned along the lateral aspect of the femur through a distally located cable sleeve oriented orthogonally to a distal femoral cable that is fixed in tension circumferentially around the femur.

It should be appreciated that the trochanter securement apparatus of various embodiments of the present disclosure may include a conduit distally linked to a plate via a tongue-in-groove mechanism. In various such embodiments, the plate can be contoured along the entire aspect of the femoral bone to facilitate fracture stability and healing.

It should be appreciated that the trochanter securement apparatus of various embodiments of the present disclosure may be employed in total shoulder replacement.

It should be appreciated that trochanteric fractures may also occur in the setting of a peri-trochanteric fracture. These fractures may consist of three of four parts. The femoral neck and shaft portion may be fixed with an intramedullary nail and lateral compression screw. The trochanteric fragment may remain free and could benefit from additional fixation to facilitate healing. Such devices frequently contain a more proximal hole in the top of the screw that can be utilized for additional threaded device.

It should be appreciated that various embodiments of the present disclosure contemplate that a proximal aspect of an intramedullary nail may be utilized to fashion a metallic suture or cable anchor. Such sutures or cables may then be passed in isolation or through a claw-shaped conduit, linking to a more distal device. This more distal device may be linked on a surgical cable or fastened to the threaded portion of a compression screw. Sutures may be tensioned around the top of the trochanter through this more distal device.

It should be appreciated that various embodiments of the present disclosure may include a distal tensioning device used to augment hip abductor repair or rotator cuff repair. In this scenario a "suture bridge" may be created by taking suture that is woven though the tendinous portion of tissue and anchored in the bone through a second anchor to create "trans-osseous equivalent" strength. Instead of placing additional suture anchors (that create weakening holes in the bone) a circumferential cable may be used to place an orthogonal tensioning sleeve. Thus, sutures from an abductor repair or rotator cuff may be may be more distally tensioned to create a "suture bridge" concept using the distal securer without making additional holes.

It should be appreciated that various embodiments of the present disclosure can be employed for "suture bridge" fixation on rotator cuff or abductor repairs.

It should be appreciated that most frequently, trochanteric fractures occur during execution of the femoral neck cut, during femoral elevation prior to broaching, or during broaching itself. It should be appreciated that various embodiments of the present disclosure contemplate the following methods (that can include one or more surgical steps) in such cases:

(A) If a trochanteric fracture is suspected or identified, one method can include removing any inserted broaches, and utilizing biplanar x-rays to ensure distal fracture extension does not exist.

(B) One method can include bringing the leg to a neutral position, and placing a single circumferential cable around the femur either just proximal or just distal to the lesser trochanter to serve as a trochanter engager securer. In such embodiments, the trochanter cable crimp/or suture securing device on this cable should be positioned lateral to the trochanter engager securer cable crimp. It should be appreciated that a location to pass the trochanter engager securer cable is often but not always, at the level of the vastus lateralis ridge. It should also be noted that a small longitudinal split of the vastus can facilitate sleeve placement and facilitate tensioning and passage of wires.

(C) One method can include tensioning and crimping the anchor cable to serve as the trochanter engager securer ensuring it is tightly wrapped around the femur without interposed soft tissue.

(D) One method can include returning to femoral broaching, selecting the stem size and neck length based upon preoperative templating, intraoperative templating, and surgeon assessment of soft tissue tension.

(E) One method can include implanting the true stem containing a threaded insertion hole.

(F) One method can include placing the threaded implant engager fastener in the femoral stem insertion hole.

(G) One method can include selecting trochanter engagement device depending on fracture size, orientation, soft tissue quality, and planned needs for mechanical constraint.

(H) One method can include placing the engagement device in the desired position, passing the cables or sutures through the medial and lateral plate holes, and passing the cables sutures around and/or through the abductor musculature.

(I) One method can include reducing the hip replacement implants, specifically the ball into the socket.

(J) One method can include retrieving the cables sutures on the lateral aspect of the femur, and checking to ensure appropriate plate position.

(K) One method can include placing the cables or sutures through the sleeve trochanter engager securer, and securing such as knotting, or applying tension and crimping.

Various changes and modifications to the present embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A direct anterior hip replacement trochanter securement apparatus comprising:
   a trochanter engager positionable to engage a trochanter of a femur of a person from an anterior position, wherein the trochanter engager includes:
      (i) a trochanter gripper including:
         (a) a connector defining a plurality of internal suture passageways, the connector configured to extend across a medial interior portion of the trochanter,
         (b) first teeth at a first end of the connector and configured to engage an anterior portion of the trochanter, and
         (c) second teeth at a second end of the connector and configured to engage a posterior portion of the trochanter, and
      (ii) a first suture, a second suture, a third suture, and a fourth suture each configured to extend through respective ones of the plurality of internal suture passageways defined by the connector to hold the trochanter gripper in place on the trochanter, at least two of the first suture, the second suture, the third suture, and the fourth suture being separate sutures;
   an implant connector configured to securely connect first portions of the first suture, the second suture, the third suture, and the fourth suture of the trochanter engager to an implant in the femur; and
   a trochanter engager securer separate from the trochanter engager and positionable on the femur at a point along the femur below the trochanter without engaging the trochanter and configured to receive and securely be connected to second portions of the first suture, the second suture, the third suture, and the fourth suture of the trochanter engager.

2. The direct anterior hip replacement trochanter securement apparatus of claim 1, wherein the implant connector includes a fastener removably connectable to the implant.

3. The direct anterior hip replacement trochanter securement apparatus of claim 1, wherein the first portions of the first suture, the second suture, the third suture, and the fourth suture are respective first ends of the first suture, the second suture, the third suture, and the fourth suture, and the second portions of the first suture, the second suture, the third suture, and the fourth suture are respective seconds ends of the first suture, the second suture, the third suture, and the fourth suture.

4. The direct anterior hip replacement trochanter securement apparatus of claim 1, wherein the trochanter engager securer includes a suture receiver, a first cable receiver connected to the suture receiver, and a cable.

5. The direct anterior hip replacement trochanter securement apparatus of claim 4, wherein the trochanter engager securer includes a second cable receiver.

6. The direct anterior hip replacement trochanter securement apparatus of claim 4, wherein the suture receiver includes a plurality of inwardly extending teeth.

7. The direct anterior hip replacement trochanter securement apparatus of claim 4, wherein the suture receiver defines openings configured to receive the first suture, the second suture, the third suture, and the fourth suture.

8. The direct anterior hip replacement trochanter securement apparatus of claim 1, wherein the plurality of internal suture passageways include a first internal suture passageway configured to receive the first suture, a second internal suture passageway configured to receive the second suture, a third internal suture passageway configured to receive the third suture, and a fourth internal suture passageway configured to receive the fourth suture.

9. The direct anterior hip replacement trochanter securement apparatus of claim 8, wherein the first internal suture passageway, the second internal suture passageway, the third internal suture passageway, and the fourth internal suture passageway are spaced apart.

10. The direct anterior hip replacement trochanter securement apparatus of claim 9, wherein the second internal suture passageway and the third internal suture passageway are spaced apart a further distance than (i) the first internal suture passageway and the second internal suture passageway, and (ii) the third internal suture passageway and the fourth internal suture passageway.

11. The direct anterior hip replacement trochanter securement apparatus of claim 1, wherein the connector is not extendable over the superior portion of the trochanter, and wherein the second suture and third suture are configured to extend over the superior portion of the trochanter.

12. The direct anterior hip replacement trochanter securement apparatus of claim 1, wherein the first teeth include two teeth configured to engage the anterior portion of the trochanter and the second teeth include two teeth configured to engage the posterior portion of the trochanter.

13. The direct anterior hip replacement trochanter securement apparatus of claim 1, wherein the plurality of internal suture passageways includes a first internal suture passageway configured to receive the first suture, a second internal suture passageway configured to receive the second suture, a third internal suture passageway configured to receive the third suture, and a fourth internal suture passageway configured to receive the fourth suture, wherein the connector is not extendable over the superior portion of the trochanter, and wherein the second suture and third suture are configured to extend over the superior portion of the trochanter.

14. The direct anterior hip replacement trochanter securement apparatus of claim 13, wherein the connector is not extendable over the superior portion of the trochanter, and wherein the second suture and third suture are configured to extend over the superior portion of the trochanter, wherein the first suture and fourth suture are configured to extend over opposite areas of the trochanter adjacent to superior portion of the trochanter.

15. The direct anterior hip replacement trochanter securement apparatus of claim 1, wherein the connector is not extendable over the superior portion of the trochanter.

\* \* \* \* \*